US006777588B2

(12) United States Patent
Waterhouse et al.

(10) Patent No.: US 6,777,588 B2
(45) Date of Patent: Aug. 17, 2004

(54) METHODS AND MEANS FOR PRODUCING BARLEY YELLOW DWARF VIRUS RESISTANT CEREAL PLANTS

(76) Inventors: Peter Waterhouse, 5 Banjine Street, O'Connor, Canberra ACT 2602 (AU); Ming-Bo Wang, 3 Kvewa Street, Kaleen, Canberra ACT 2617 (AU); David Abbott, 39 Macleay Street, Turner, Canberra ACT 2612 (AU)

( * ) Notice: Subject to any disclaimer, the term of this patent is extended or adjusted under 35 U.S.C. 154(b) by 63 days.

(21) Appl. No.: 09/984,863

(22) Filed: Oct. 31, 2001

(65) Prior Publication Data

US 2002/0169298 A1 Nov. 14, 2002

Related U.S. Application Data

(60) Provisional application No. 60/244,209, filed on Oct. 31, 2000.

(51) Int. Cl.[7] ........................ C12N 15/82; C12N 15/90; A01H 1/00; A01H 5/00

(52) U.S. Cl. .................... 800/280; 435/320.1; 435/468; 800/260

(58) Field of Search ............................. 435/320.1, 419, 435/468; 800/278, 280, 260, 298, 320, 320.3

(56) References Cited

FOREIGN PATENT DOCUMENTS

| | | | |
|---|---|---|---|
| WO | WO 98/53083 | 11/1998 | ........... C12N/15/63 |
| WO | WO 99/32619 | 7/1999 | ........... C12N/15/11 |
| WO | WO 99/49029 | 9/1999 | ........... C12N/15/11 |
| WO | WO /99/53050 | 10/1999 | ........... C12N/15/11 |
| WO | WO /99/61631 | 12/1999 | ........... C12N/15/63 |
| WO | WO 00/49035 | 8/2000 | ........... C07H/21/04 |

OTHER PUBLICATIONS

Tenllado et al., MPMI, 2003, vol. 16, pp. 149–158.*

Vionnet, O., Trends Genet., Aug. 2001, vol. 17, pp. 449–459.*

Tingay et al., Plant J., 1997, vol. 11, pp. 1369–1376.*

Barker, H. et al, "The Development of Resistance to Luteoviruses Mediated by Host Genes and Pathogen–Derived Transgenes", *The Luteoviridae*, 1999, pp. 169–210, (Smith, H.G. and Barker, H., eds), CABI Publishing, Wallingford, United Kingdom.

Burnett, P.A. et al, "Host Plant Tolerance of Resistance for Control of Barley Yellow Dwarf", 1995, *Barley Yellow Dwarf: 40 Years of Progress*, pp. 321–343, (D'Arcy, C.J. and Burnett, P.A., eds) APS press, St. Paul, MN, USA.

Hamilton, A.J. et al, "A Species of Small Antisense RNA in Posttranscriptional Gene Silencing in Plants" *Science*, Oct. 29 1999, pp. 950–952, vol. 286, American Association for the Advancement of Science, Washington, D.C.

Kawchuck, L.M. et al, "Field Resistance to the Potato Leafroll Luteovirus in Transgenic and Somaclone Potato Plants Reduces Tuber Disease Symptoms", *Can. J. Plant Pathol.*, 1997, pp. 260–266, published quarterly at Ottawa, Ontario by the Canadian Phytopathological Society.

Koev, G. et al, "Extreme Reduction of Disease in Oats Transformed With the 5' half of the Barley Yellow Dwarf Virus–PAV Genome", *Phytopathology*, 1998, pp. 1013–1019, vol. 88, No. 10, The American Phytopathological Society, Ames, Iowa.

Lagudah, E.S. et al, "The Molecular–Genetic Analysis of *Triticum tauschii*–the D Genome Donor to Hexaploid Wheat", *Genome*, 1991, pp. 375–386, vol. 34 (3), National Research Council of Canada, Ottawa, Canada.

Larkin, P.J. et al, "The Yd2 Resistance to Barley Yellow Dwarf Virus is Effective in Barley Plants but not in Their Leaf Protoplasts", *Ann. Appl. Biol* 1991, pp. 115–125, vol. 118, Association of Applied Biologists, London, England.

Lister, R.M. et al, "Distribution and Economic Importance of Barley Yellow Dwarf", *Barley Yellow Dwarf: 40 Years of Progress*, 1995, pp. 29–53, (D'Arcy, C.J. and Burnett, P.A. eds) APS Press, St. Paul, MN, USA.

Mayo, M.A. et al, "Family Luteoviridae: a Reclassification of Luteoviruses", *The Luteoviridae*, 1999, pp. 15–22, (Smith, H.G. and Barker, H., eds) CABI publishing, Wallingford, United Kingdom.

Martin, R.R. et al, "Evolution and Molecular Biology of Luteoviruses", *Annual Review of Phytopathology*, 1990, pp. 341–363, vol. 28, Annual Reviews, Inc. Palo Alto, California.

Martin, R.R. et al, "Taxonomy of Barley Yellow Dwarf Viruses", *Barley Yelow Dwarf: 40 Years of Progress*, 1995, pp. 203–214, (D'Arcy, C.J. and Burnett, P.A. eds) APS Press, St. Paul, MN, USA.

McGrath, P.F. et al, "Coat Protein–Mediated Resistance to Isolates of Barley Yellow Dwarf in Oats and Barley", *Eur. J. Pathol.*, 1997, pp. 695–710, vol. 103, Kluwer Academic Publishers, Netherlands.

Miller, W.A. et al, "Sequence and Organization of Barley Yellow Dwarf Virus Genomic RNA", *Nucleic Acids Research*, 1988, pp. 6097–6111, vol. 16, No. 13, IRL Press Limited, Oxford, England.

Miller, W.A. et al, "Luteovirus Gene Expression", *Crit. Rev. Plant Sci.*, 1995, pp. 179–211, vol. 14, No. 3, CRC Press, Inc. Boca Raton, Florida USA.

(List continued on next page.)

*Primary Examiner*—Ashwin Mehta
(74) *Attorney, Agent, or Firm*—Burns, Doane, Swecker & Mathis, L.L.P.

(57) ABSTRACT

The invention relates to methods for producing transgenic cereal plants resistant to Barley Yellow Dwarf Virus, particularly in the presence of co-infecting Cereal Yellow Dwarf Virus, by stably integrating into the cells of the transgenic plant a chimeric gene comprising a DNA region operably linked to plant expressible promoter in such a way that the RNA molecule may be transcribed from the DNA region, the RNA molecule comprising both sense and antisense RNA capable of pairing and forming a double stranded RNA molecule or hairpin RNA.

20 Claims, 6 Drawing Sheets

OTHER PUBLICATIONS

Paltridge, N.G. et al, "Development of YLM, a Codominant PCR Marker Closely Linked to the Yd2 Gene for Resitance to Barley Yellow Dwarf Disease", *Theor. Appl. Genet.*, 1998, pp. 1170–1177, vol. 96, Springer–Verlag, Berlin, Germany.

Presting, G.G. et al, "Resistance to Potato Leafroll Virus in Potato Plants Transformed with the Coat Protein or with Vector Control Constructs" *Phytopathology* 1995, pp. 436–441, vol. 85, American Phytopathological Society, St. Paul, Minn.

Pruss, G. et al, "Plant Viral Synergism: The Potyviral Genome Encodes a Broad–Rang Pathogenicity Enhancer that Transactivates Replication of Heterologous Viruses", *The Plant Cell*, Jun. 1997, pp. 859–868, vol. 9, American Society of Plant Physiologists, Rockville, Maryland Rasmusson, D.C. et al, "Inheritance of Resistance in Barley to the Yellow–Dwarf Virus", *Agronomy Journal*, 1959, pp. 661–664, vol. 51, American Society of Agronomy, Madison, Wisconsin.

Schaller, C.W. et al, "The Inheritance and Linkage of the Yd2 Gene Conditioning Resistance to Barley Yellow Dwarf Virus Disease in Barley", *Crop Sci.*, 1964, pp. 544–548, vol. 4, Crop Science Society of America, Madison, Wisconsin.

Schaller, C.W. "The Genetics of Resistance to Barley Yellow Dwarf Virus in Barley", *Barley Yellow Dwarf: The Proceedings of a Workshop* (Burnett, P.A., 85), 1984, pp. 93–99, CIMMYT, Mexico.

Sharp, P.A. et al, "RNA Interferences", *Science*, Mar. 31, 2000, pp. 2431 and 2433, vol. 287, American Association for the Advancement of Science with the assistance of Stanford University's Highwire Press, Stanford, California USA.

Shi, X.M. et al, "Mutations in the Region Encoding the Central Domain of Helper Component–Proteinase (HC–Pro) Eliminate Potato Virus X/Potyviral Synergism", *Virology*, 1997, pp. 35–42, vol. 231, article No. VY978488, Academic Press, San Diego, California.

Singh, et al, "*BDV1*: A Gene for Tolerance to Barley Yellow Dwarf Virus in Bread Wheats", 1993, *Crop Sci*pp. 231–234, vol. 33, Crop Science Society of America, Madison, Wisconsin.

Smith, N.A. et al, "Total Silencing by Intron–Spliced Hairpin RNAs", *Nature*, Sep. 2000, pp. 319–320, vol. 407, Nature Publishing Group, Hampshire, United Kingdom.

Tingay, S. et al, "*Agrobacterium tumefaciens*–mediated Barley Transformation", *The Plant Journal*, 1997, pp. 1369–1376, vol. 11, No. 6, Blackwell Sciences Ltd., Oxford, England.

Tuschl. T. et al, "Targeted mRNA Degradation by Double–Stranded RNA in Vitro", *Genes & Development*, 1999, pp. 3191–3197, vol. 13, Cold Spring Harbor Laboratory Press, Cold Spring Harbor, New York.

Vance, V.B. et al, "5' Proximal Potyviral Sequences Mediate Potato Virus X/Potyviral Synergistic Disease in Transgenic Tobacco", *Virology*, 1995, pp. 583–590, vol. 206, Academic Press, Inc., San Diego, California.

Voinnet, O. et al, "Suppression of Gene Silencing: A General Strategy Used by Diverse DNA and RNA Viruses of Plants", *PNAS*, Nov. 23, 1999, pp. 14147–14152, vol. 96, No. 24, National Academy of Sciences, Washington, DC USA.

Vance, V.B. et al., "Replication of Potato Virus X RNA is Altered in Coinfections with Potato Virus Y", Virology, 1991, pp. 486–494, vol. 182, Academic Press, Inc., San Diego, California.

Wang, M.B. et al, Comparison of the Coat Protein, Movement Protein and RNA Polymerase Gene Sequences of Australia, Chinese, and American Isolates of Barley Yellow Dwarf Virus Transmitted by *Rhopalosiphum Padi, Archives of Virology*, 1998, pp. 1005–1013, vol. 143, Springer–Verlag, Austria.

Wang, M.B. et al, "High–efficiency Silencing of a β–flucuronidase Gene in Rice is Correlated with Repetitive Transgene Structure but is Independent of DNA Methylation", *Plant Molecular Biology*, 2000, pp. 67–82, vol. 43, Kluwer Academic Publishers, Netherlands.

Wang, M.B. et al, "Improved Vectors for *Agrobacterium tumefaciens*—Mediated Transformation of Monocot Plants", 1998, *Acta Hort.*, pp. 401–407, ISHS Act Horticulturae 461: International Symposium on Biotechnology of Tropical and Subtropical Species Part 2.

Waterhouse, P.M., et al "Virus Resistance and Gene Silencing in Plants Can be Induced by Simultaneous Expression of Sense and Antisense RNA", *Proc. Natl. Acad. Sci. USA*. Nov. 1998, pp. 13959–13964, vol. 95, National Academy of Sciences, Washington, D.C, USA.

Waterhouse, P.M. et al, "Virus Resistance and Gene Silencing: Killing the Messenger", *Trends in Plant Science*, Nov. 1999, pp. 452–457, vol. 4, No. 11, Elsevier Science Ltd, Oxford, United Kingdom.

Waterhouse, P.M. et al, "Serotype–Specific and General Luteovirus Probes from Cloned cDNA Sequences of Barley Yellow Dwarf Virus", *J. Gen. Virol.*, 1986, pp. 1273–1281, vol. 67, Society for General Microbiology, London, England.

Waterhouse, P.M. et al, "AAB Descriptions of Plant Viruses", Sep. 1988, No. 339, The Luteovirus Group, Institute of Horticultural Research, Wellesbourne, Warwick, United Kingdom.

Waterhouse, P.M., et al, "Genetic Engineering of Virus Resistance", 1998, *Molecular Biology of Rice*, pp. 257–281, (Shimamoto, K., ed) Springer–Verlag, Tokyo.

Xin, Z.Y. et al, "Characterization of a Potential Source of Barley Yellow Dwarf Virus Resistance for Wheat", 1988, *Genome*, pp. 250–257, vol. 30, National Research Council of Canada, Ottawa, Canada.

Zamore, P.D. et al, "RNAi: Double–Stranded RNA Directs the ATP–Dependent Cleavage of mRNA at 21 to 23 Nucleotide intervals", *Cell*, Mar. 31, 2000, pp. 25–33, vol. 101, Cell Press, Cambridge, Massachusetts USA.

Christensen and Quail, "Uniquitin Promoter–Based Vectors for High–Level Expression of Selectable and/or Screenable Marker Genes in Monocotyledonous Plants", 1996, *Transgenic Research*, pp. 213–218, vol. 5, Kluwer academic Publishers, London, UK.

Michael T. McManus, et al., "Gene Silencing in Mammals by Small Interfering RNAs," Nature Reviews, vol. 3, Oct. 2002, pp. 737–747.

Guilang Tang, et al, "A biochemical framework for RNA silencing in plants," Genes & Development, vol. 17, pp. 49–63.

Jenn–Yah Yu, et al., "Simultaneous Inhibition of GSKαand GSK3βUsing Hairpin siRNA Expression Vectors," Molecular Therapy, vol. 7, No. 2, Feb. 2003, pp. 228–236.

P.F. McGrath, et al., "Coat protein–mediated resistance to isolates of barley yellow dwarf in oats and barley," European Journal of Plant Pathology, vol. 103, 1997, pp. 695–710.

Gennadiy Koev, et al, "Extreme Reduction of Disease in Oats Transformed with the 5' Half of the Barley Yellow Dwarf Virus–PAV Genome," Virology, vol. 88, No. 10, 1998, pp. 1013–1019.

Ming–Bo Wang, et al., "*Agrobacterium tumefaciens*—mediated transformation of an elite Australian barley cultivar with virus resistance and reporter genes," Aust. J. Plant Physiol., vol. 28, 2001, pp. 149–156.

* cited by examiner

A

B

SEQUENCE LISTING

<160> NUMBER OF SEQ ID NOS: 9

<210> SEQ ID NO 1
<211> LENGTH: 1594
<212> TYPE: DNA
<213> ORGANISM: Barley yellow dwarf virus
<220> FEATURE:
<221> NAME/KEY: misc_feature
<223> OTHER INFORMATION: part of BYDV genome spanning ORF1 and 5' end of ORF2

<400> SEQUENCE: 1
ttttcgaaat acttatagga gctagcgcta aggcggtcaa agacttcatc agccattgtt 60
actctcgttt gaaatctata tattattctt tcaaacgatg gctgatggag atatctgggc 120
agtttaaggc ccacgacgcc tttgtcaaca tgtgcttcgg gcacatggct gacattgagg 180
acttcgaggc agagctcgct gaggagtttg ccgagaggga ggatgaggtg gaagaggcaa 240
ggagcctctt gaaactgctg gttgcccaaa aatctaaaac tggggtaacc gaggcttgga 300
ccgacttctt tacgaagtcg agaggtggcg tctatgcgcc actttcctgc gagcctacca 360
ggcaggagct agaagctaag agcgagaagc tcgaaaagct tctagaagaa cagcaccaat 420
tcgaggtgcg agcggccaag aaatacatta aggaaaaagg ccgcggcttc atcaactgtt 480
ggaacgactt gcgaagtcgt ctcaggctgg tgaaggacgt caaggacgag gcgaaggaca 540
acgccagagc tgctgccaag atcggagcag aaatgttcgc ccccgttgac gtgcaagacc 600
tctacagttt cacagaggtc aagaaggtgg agaccggcct catgaaggag gtcgtgaaag 660
agagaaacgg cgaagaagag aaacacctcg agcccatcat ggaagaggtg agatctatca 720
aggacaccgc tgaagctagg gacgccgcct ccacttggat aacagagaca gttaagctga 780
agaattctac gcttaatgcc gatgaattgt ctctggccac catcgcccgc tacgtcgaaa 840
acgtagggga caaattcaaa ctcgacattg ctagcaagac atatctaaag caagtcgcat 900
cgatgtctgt accaattcca actaacaagg acatcaaatt gaagatggtg ctgcagagtc 960
ctgaagcacg tgccaggcgg gaaccgttgg acgtgcttga ctctgtgggt ttttagaggg 1020
gctctgtacc gcctctggtt ttgagagccc attccctatt ctcgggctgc cagagattgc 1080
ggtcacagac ggagcccggc tccgtaaggt tagtagtaat attagatacc ttagccaaac 1140
ccacctaggt cttgtatata aggcaccaaa tgcctccctg cacaatgcgc ttgtagcagt 1200
ggagagaaga gttttcacag taggaaaggg ggacaaagca atctaccccc cccgcccaga 1260
gcatgacatt ttcactgata caatggatta cttccaaaaa tccattatag aagaggtggg 1320
atactgtaga acatatccag cgcaactcct ggctaacagc tatagcgcag gaaagagagc 1380
catgtatcac aaagccattg catcattgag gactgtccct tatcatcaga aggatgctaa 1440
tgtgcaagct ttcctgaaga aggaaaaaca ctggatgacc aaggacatcg ccccccgatt 1500
gatttgcccc cgcagcaagc ggtacaacat catcctagga actcgtttga aattcaacga 1560

-continued

```
gaagaagatc atgcacgcta tcgatagtgt gttc                            1594


<210> SEQ ID NO 2
<211> LENGTH: 986
<212> TYPE: DNA
<213> ORGANISM: Barley yellow dwarf virus
<220> FEATURE:
<221> NAME/KEY: misc_feature
<223> OTHER INFORMATION: part of BYDV genome spanning the 3' end of ORF2

<400> SEQUENCE: 2

ggatccccca ctgtgctttc tggctatgac aactttaaac aaggaagaat catagccaag     60

aagtggcaaa agtttgcatg ccccgtcgcc atcggcgtgg atgctagccg ctttgaccaa    120

cacgtgtcag agcaggcgct taagtgggaa cacgggatat acaatgggat cttcggagac    180

agcgaactgg ctcttgcact tgaacatcaa atcaccaaca acatcaagat gtttgttgaa    240

gataaaatgc ttaggttcaa ggtaaggggc cacagaatgt ccggtgacat taataccagc    300

atgggaaata agctcataat gtgcggcatg atgcatgcat atttcaagaa gctgggtgtt    360

gaagctgaac tttgtaacaa cggagacgac tgtgtcatca tcactgatag agccaatgag    420

aagctctttg atggcatgta cgaccatttc ctccagtatg gcttcaacat ggtgaccgaa    480

aaaccagttt acgaactgga gcaattggag ttttgccagt caaaaccggt ctctattaat    540

ggaaagtata gaatggtcag aaggcccgat agcataggca aagatagcac aacactactg    600

agcatgctca atcaatccga cgtcaagagc tacatgtcgg ctgttgctca gtgtggcctg    660

gtgctcaacg ctggagtacc catacttgaa agtttctata aatgcctata tagaagctcg    720

gggtacaaga aagtgagtga ggaatttatt aaaaacgtca tatcgtatgg aacagatgag    780

agactacaag gtagacgtac ctataatgaa acacctatca caaaccacag tagaatgtcc    840

tactgggaat cattcggagt tgaccctaag atacagcaaa tcgtcgagag gtactacgac    900

ggtcttacgg taagtgccca actccagagc gtgaaggtga cgactccaca tctgcaatca    960

atactacttt ccataccgga aaacca                                          986


<210> SEQ ID NO 3
<211> LENGTH: 65
<212> TYPE: DNA
<213> ORGANISM: Artificial sequence
<220> FEATURE:
<223> OTHER INFORMATION: oligonucleotide primer 1

<400> SEQUENCE: 3

accattctat tgtgctctcg cacagagata agcaggaaac catggttttc gaaatactaa     60

taggt                                                                  65


<210> SEQ ID NO 4
<211> LENGTH: 28
<212> TYPE: DNA
<213> ORGANISM: artificial sequence
<220> FEATURE:
<223> OTHER INFORMATION: oligonucleotide primer 2

<400> SEQUENCE: 4

ccggaattct taatattcgt tttgtgag                                         28


<210> SEQ ID NO 5
<211> LENGTH: 20
<212> TYPE: DNA
<213> ORGANISM: artificial sequence
```

-continued

<220> FEATURE:
<223> OTHER INFORMATION: oligonucleotide primer 3

<400> SEQUENCE: 5
tgtggcagtg gagagaagag 20

<210> SEQ ID NO 6
<211> LENGTH: 20
<212> TYPE: DNA
<213> ORGANISM: artificial sequence
<220> FEATURE:
<223> OTHER INFORMATION: oligonucleotide primer 4

<400> SEQUENCE: 6
atgttgttgg tgatttggtg 20

<210> SEQ ID NO 7
<211> LENGTH: 5677
<212> TYPE: DNA
<213> ORGANISM: Barley yellow dwarf virus
<220> FEATURE:
<221> NAME/KEY: misc_feature
<222> LOCATION: (1)..(1)
<223> OTHER INFORMATION: "n" = a,g,c,or t
<300> PUBLICATION INFORMATION:
<308> DATABASE ACCESSION NUMBER: Genbank/X07653
<309> DATABASE ENTRY DATE: 1995-06-12
<313> RELEVANT RESIDUES: (1)..(5677)

<400> SEQUENCE: 7
ngtgaagatt gaccatctca caaaagctgt tacgtgcttg taacacacta cgcgcccgtt 60
ttgtattcgg gaagtagttg cgaaaacggt ccccttattg cctgacaagc taagggccac 120
ccttctttcc ccaccgccat catgtttttc gaaatactaa taggtgctag cgccaaggcg 180
gtcaaagact tcattagcca ttgctattct agattgaaat ctatatacta ttctttcaag 240
cgatggctaa tggagatatc agggcaattt aaggcccacg acgcctttgt caacatgtgc 300
tttgggcaca tggctgacat tgaggacttc gaggcggaac tcgctgagga gttcgccgag 360
agggaggatg aggtggaaga ggcgaggagc ctcttgaaac tgctggtcgc ccaaaaatct 420
aaatctgggg tgaccgaggc ttggaccgac ttttttacaa agtcgagagg tggtgtttac 480
gcaccacttt cctgcgagcc taccaggcag gagctagaag tcaagagtga gaaactcgag 540
cgacttctag aagagcagca ccaatttgag gtgcgagcgg ccaagaaata catcaaggaa 600
aagggccgcg gcttcatcaa ctgctggaac gacttgcgga gtcgtctcag gttggtgaag 660
gacgtcaagg acgaggcgaa ggacaacgcc agagctgctg ccaagattgg agcagaaatg 720 ttcgccccctg ttgacgtgca ggacctctac agtttcacgg aggtcaagaa ggtggagacc 780
ggcctcatga aggaggtcgt gaaagagaaa aacggcgaag aagagaaaca cctcgaaccc 840
atcatggaag aggtgaggtc catcaaggac accgccgaag ccagggacgc cgcctccact 900
tggataacag agacagttaa gctgaagaac gcaacgctta acgcagatga actgtctctt 960
gccaccatcg cccgctacgt tgaaaacgta ggggacaagt tcaaactcga cattgctagt 1020
aaaacatatc taaagcaagt cgcatcgatg tctgtaccaa ttccaaccaa caaagacatc 1080
aaattgaaga tggtgctaca gagtcctgaa gcacgtgcca ggcgggaacg catggacgtg 1140
cttgactctg tgggttttta gaggggctct gtaccgcctc tggttttgag agcccattcc 1200
ctattctcgg gctgccagag attgcggtca cagacggagc ccggctccgc aaggttagta 1260
gcaatattag ataccttagc caaacccatc taggtcttgt atataaggca ccaaatgcct 1320

-continued

```
ccctgcacaa cgcgcttgtg gcagtggaga gaagagtttt tacagtagga aagggggaca   1380
aggcaatcta cccccccgc cctgagcatg acattttcac tgatacgatg gattactttc    1440
aaaaatccat tatagaagag gtgggatact gtaaaacata tccagcgcaa ctcctggcta   1500
atagctatag cgcaggaaag agggccatgt atcacaaagc cattgcatcc ttgaaaactg   1560
tcccatatca tcagaaggat gccaatgtgc aagctttcct gaagaaggaa aaacattgga   1620
tgaccaagga catcgccccc cgattgattt gcccccgcag caagcggtat aatatcatcc   1680
taggaactcg tttgaaattc aacgagaaga agatcatgca cgccatcgat agtgtgtttg   1740
gatcccccac tgtgctttct ggttatgaca acttcaaaca aggaagaatc atagccaaaa   1800
agtggcaaaa gtttgcatgc cccgtcgcca tcggcgtgga tgctagccgc tttgaccaac   1860
atgtgtcaga gcaggcgctt aagtgggaac acgggatata caatggaatc ttcggagaca   1920
gcgaaatggc tcttgcactt gaacaccaaa tcaccaacaa catcaagatg tttgttgaag   1980
acaaaatgct taggttcaag gtaagaggcc acagaatgtc cggtgacatt aataccagca   2040
tgggaaataa gctcataatg tgcggcatga tgcacgcata tcttaagaag ctgggtgttg   2100
aagctgaact atgtaataac ggagacgact gtgtcatcat cactgataga gccaatgaga   2160
agctctttga tggcatgtac gaccatttcc tccagtatgg cttcaacatg gtgaccgaaa   2220
aaccagttta cgaactggaa caattggagt tttgccagtc aaaaccggtc tctattaatg   2280
gaaagtatag aatggtcaga aggcccgata gcataggcaa agatagcaca acactactga   2340
gcatgctcaa tcaatccgac gtcaagagct acatgtcggc tgtcgctcag tgtggtttgg   2400
tgctcaacgc tggagtaccc atacttgaaa gtttctataa atgcctatat aggagctcgg   2460
ggtacaaaaa agtgagtgag gaatttatta aaaacgtcat atcgtatgga acagatgaga   2520
gactacaagg tagacgtacc tataatgaaa cacctatcac aaaccacagt agaatgtcct   2580
actgggaatc attcggagtt gaccctaaga tacagcaaat cgtcgagagg tactacgacg   2640
gtcttacggt aagtgcccaa ctccagagtg tgaaggtgac gactccacat ctgcaatcaa   2700
tactgctttc cataccggaa aaccactcac aaaacgaata ttaattacca aatcttagct   2760
gggtttggga tagggtttat agttagtata ccctgtacat tagctctcgc gtactttatt   2820
tacaataaag tttcagacac cactagagag gtggtgaatg aattcagtag gtcgtagagg   2880
acctagacgc gcaaatcaaa atggcacaag aaggaggcgc cgtagaacag ttcggccagt   2940
ggttgtggtc caacccaatc gagcaggacc cagacgacga aatggtcgac gcaagggaag   3000
aggaggggca aattttgtat ttagaccaac aggcgggact gaggtattcg tattctcagt   3060
tgacaacctt aaagccaact cctccggggc aatcaaattc ggccccagtc tatcgcaatg   3120
cccagcgctt tcagacggaa tactcaagtc ctaccatcgt tacaagatca caagtatccg   3180
agttgagttt aagtcacacg cgtccgccaa tacggcaggc gctatcttta ttgagctcga   3240
caccgcgtgc aagcaatcag ccctgggtag ctacattaat tccttcacca tcagcaagac   3300
cgcctccaag accttccggt cagaggcaat taatgggaag gaattccagg aatcaacgat   3360
agaccaattt tggatgctct acaaggccaa tggaactacc actgacacgg caggacaatt   3420
tatcattacg atgagtgtca gtttgatgac ggccaaatag gtagactcct caacaccgga   3480
accaaaacct gcaccggaac caacaccaac cccccagcca acgccggctc cacagcccac   3540
acctgaacca actcctgcac ctgtccccaa aagattcttc gagtatatcg gaactcctac   3600
cggtacaatc tcgactagag agaacactga cagtatatct gtcagcaagc tcggtggaca   3660
gtcgatgcag tacattgaga atgagaaatg tgaaacgaaa gtcatcgatt ccttttggag   3720
```

-continued

```
cactaacaac aacgtttctg cgcaagcagc tttcgtttat ccagtgccag agggatcata   3780
cagcgttaac atttcgtgcg aaggcttcca gtcagttgac cacatcggtg gcaacgagga   3840
cggctattgg attggtttaa ttgcctactc caattcgtct ggcgataatt ggggagttgg   3900
caattacaaa gggtgcagtt ttaagaattt cttggcaacc aacacttgga gaccaggcca   3960
caaagatctc aagttgactg attgccagtt cacagatgga caaatagttg aaagggacgc   4020
cgtgatgtct ttccacgtag aagcaacagg caaggatgcc agcttctacc tcatggctcc   4080
caaaacaatg aaaactgaca aatacaacta tgttgtctca tatggagggt acacaaacaa   4140
gcgaatggaa ttcggtacca tatctgtgac atgtgatgaa tccgatgttg aggcagaacg   4200
aataacaagg cacgctgaaa cgcccatacg ttctaaacat attcttgttt ctgagcggta   4260
tgcggaacca ttgcccacca tagtcaacca aggcttgtgt gatgtgaaaa ctcccgagca   4320
agaacaaaca ctggtggatg aagatgacag acaaactgtt tctactgaat ctgatatagc   4380
actcctggag tatgaggctg caacagctga gattccggat gctgaagagg acgttttgcc   4440
ctccaaggaa cagttgtctt caaaaccaat ggatacgtct ggcaatataa taccaaaacc   4500
caaggaacct gaagtacttg ggacatacca aggacagaac atttatcctg aagacgtacc   4560
tccaatggcg cggcagaaat tgagagaagc cgcgaatgcg ccttccacgc tactctatga   4620
aagaagaacc ccaaagaaga gtggcaactt tttatccaga cttgtagaag cgaataggtc   4680
ccctactact cccactgccc catccgtgtc aactacttca aacatgacaa gggagcagct   4740
ccgggagtac actaggatta gaaattccag cggaatcaca gcagcaaagg cgtacaaggc   4800
gcaattccag tgaagacaac accactagca caaatcggat cctgggaaac aggcagaact   4860
tcggttcgta agctcgggta ggccgtcaac ctaccgccgt atcgtattgt gtttggccga   4920
tggaggatct tcacgttatc gccgtttgta ttcttgcttt gactgtgctc tctggggtag   4980
gcgctgtttt gagttgctgc cgttggtgct gcagcaatcc ttttcctccc tccctctctt   5040
ctgttcaagc aaaagactct cgatctgtgc gagagacaat caaaaatatc gagggagctt   5100
cggctcagtg aggggattaa cgacccccag taatggccgg tcctggcgga cataaataac   5160
ccgctatagg acgaagtggt agccaccact gatcaaatgg caaacatgct tctgtgttgt   5220
acactgcccc ggagcctacc gggtcaacaa ggctatccca ccaacccgat gaaatgaggg   5280
tggagtgagc ggagtgggtg acttcgtgat gtacacccga tcgtcaggat tgaagacgtt   5340
aaaactcgac gacctggtac aagtcgttaa actgactcgg gtggatacac cacacccggc   5400
ccagcatgtt ggcataccca cgatacgaaa cgtgggtctc ttggagccac tacctgtgat   5460
gcaaggtagg gtatgagtct tagcaagctc tgagccagga gatggacata aaccatagca   5520
atccaacgtg taaccgcaat ggggcaaaca acaggtgaac cgtgtccacg ggcctggtta   5580
ccgaaaggaa agccagtatc caacacagca atgtgttggg ggtcacacct tcggggtact   5640
cttaacgctg acactcgaaa gagcagttcg gcaaccc                            5677
```

<210> SEQ ID NO 8
<211> LENGTH: 196
<212> TYPE: DNA
<213> ORGANISM: Cereal Yellow Dwarf Virus

<400> SEQUENCE: 8

```
ccgaggacca agtcgaaagt tttatcaatg tcctcgcggg taccgctggt gcccgtcctg     60
atgagatctg cgacaagtgg cgcgatctct tggttccaac ggactgctct ggtttcgact    120
```

-continued

```
ggtcagtctc cgattggatg ctcgcagacg atatggaggt aagaaatcct cttaccatcg    180

actgcaatga gctcac                                                    196


<210> SEQ ID NO 9
<211> LENGTH: 195
<212> TYPE: DNA
<213> ORGANISM: Cereal Yellow Dwarf Virus

<400> SEQUENCE: 9

gttcacacat cttcaagtct cctaccctcg ccattccggt caatgccaac aagatattgt     60

accgcttgat ccacgggtac aatccggaat gtggaaacgc tgaggtgatt gtcaattacc    120

tcaatgcagc cagctcagtg ctgcatgagc tccgtcatga tcaggagctt tgcgcgttat    180

tgcatatgtg gttag                                                     195
```

METHODS AND MEANS FOR PRODUCING BARLEY YELLOW DWARF VIRUS RESISTANT CEREAL PLANTS

CROSS-REFERENCE TO RELATED APPLICATIONS

This application is a continuation-in-part of U.S. Provisional Application Serial No. 60/244,209, filed Oct. 31, 2000, the contents of which are incorporated herein by reference.

FIELD OF THE INVENTION

The invention relates to methods for producing transgenic cereal plants resistant to Barley Yellow Dwarf Virus, particularly in the presence of co-infecting Cereal Yellow Dwarf Virus, by stably integrating into the cells of the transgenic plant a chimeric gene comprising a DNA region operably linked to plant expressible promoter in such a way that a RNA molecule may be transcribed from the DNA region, the RNA molecule comprising both sense and antisense RNA capable of pairing and forming a double stranded RNA molecule or hairpin RNA.

DESCRIPTION OF RELATED ART

Barley yellow dwarf virus-PAV (BYDV-PAV) is the most serious and widespread virus of cereals worldwide. The barley yellow dwarf virus (BYDV), also called red leaf in oats, can infect barley, oats, rye and wheat as well as numerous species of grasses. It occurs in most parts of the world and is considered the most common viral disease of cereal crops.

BYDV (and CYDV) have been reported to cause cereal disease in over 50 countries. In almost all cases where the species has been determined, the major losses have been due to BYDV-PAV (Barker & Waterhouse, 1999). Lost production due to BYDV averages about 15% in barley, 17% in wheat and 25% in oats (Lister and Ranieri, 1995). BYDV infection can affect plant height, grain size and grain quality. For example, BYDV infection of barley can reduce the grain quality such that it is suitable only for animal feed rather than malting.

BYDV is transmitted by several species of aphids. As the aphids (winged or wingless) feed on the cereal crop, they transmit the virus through their mouthparts. The aphids can remain infectious for life, which is around 40 days.

Disease symptoms vary with the host species and the stage of crop development. Infections at the seedling stage may result in death or dwarfing as well as sterile heads. Leaves turn yellow from the tip down, along the leaf margins or in blotchy patches. Infected barley leaves, particularly flag leaves, turn bright yellow. In oats, the leaves may turn from red to purple. Discolored areas enlarge and progress to the base of the plant. Heads may be wholly or partially sterile. There may also be an increase or decrease of tillers produced by infected plants. Cereal plants infected early in the season may be shaded out by healthy or late infected surrounding plants. Winter wheat seedlings may be 100 percent infected with BYDV before freeze-up in the fall. BYDV affects yields by stunting, reduced tillering, sterility, and failure to fill kernels.

Natural resistance genes against this luteovirus give inadequate control. Sources of natural resistance to BYDV and CYDV are rare (for reviews see Barker and Waterhouse 1999; Burnett et al., 1995). In barley, the Yd2 gene (Paltridge et al., 1998), originally identified in Ethiopian concessions (Rasmussin and Schaller, 1959; Schaller et al., 1964), can confer resistance against BYDV-PAV, but its effectiveness varies depending on the genetic background of the plant and growth conditions (Schaller, 1984; Larkin et al., 1991). The Bdv1 gene confers some tolerance to BYDV (Singh et al, 1993) and has been introduced into some wheat cultivars, such as Anza. However, BYDV replicates and causes symptoms and yield loss in plants containing either the Yd2 or Bdv1 genes.

Previous attempts to introduce synthetic resistance into cereals have produced variable results. Virus resistance in plants containing virus-derived transgenes, usually by the expression of functional or dysfunctional coat protein, movement or polymerase genes, has been widely reported (for review see Waterhouse & Upadhyaya 1998) and attempts have been made to produce transgenic plants with resistance to a few different luteoviruses, by expression of coat protein and polymerase genes.

McGrath et al. (1997) transformed oat and barley plants with transgenes derived from the coat protein genes of BYDV-PAV and CYDV-RPV and obtained some resistant plants. However, this resistance was not stable.

In another study, Koev et al. (1998) transformed oat plants with the 5'half of the BYDV-PAV genome and found one line that after inoculation with BYDV-PAV showed disease symptoms but recovered and produced seed. Although BYDV resistance in the progeny of this line was inherited, the levels of resistance varied greatly among individual plants, ranging from substantial to undetectable.

Waterhouse et al., 1998, Wang & Waterhouse, 2000 and Smith et al., 2000 describe that virus immunity and post-transcriptional gene silencing (PTGS) can be induced in plants using transgenes that encode double stranded (ds) or self-complementary "hairpin" (hp) RNA.

WO 98/53083 describes constructs and methods for enhancing the inhibition of a target gene within an organism involve inserting into the gene-silencing vector an inverted repeat sequence for all or part of a polynucleotide region within the vector. The inverted repeat sequence may be a synthetic polynucleotide sequence or comprise a modified natural phenotype.

WO 99/32619 provides a process of introducing RNA into a living cell to inhibit gene expression of a target gene in that cell. The RNA has a region with a double-stranded structure. Inhibition is sequence-specific in that the nucleotide sequence of the duplex region of the RNA and of a portion of the target gene are identical.

WO 99/49029 relates to a method of modifying gene expression and to synthetic genes for modifying endogenous gene expression in a cell, tissue or organ of a transgenic organism, in particular a transgenic animal or plant. Recombinant DNA technology is used to post-transcriptionally modify or modulate the expression of a target gene in a cell, tissue, organ or whole organism, thereby producing novel phenotypes. Synthetic genes and genetic constructs which are capable of repressing, delaying or otherwise reducing the expression of an endogenous gene or a target gene in an organism when introduced thereto are also provided.

WO 99/53050 provides methods and means for reducing the phenotypic expression of a nucleic acid of interest in eukaryotic cells, particularly in plant cells, by introducing chimeric genes encoding sense and antisense RNA molecules directed towards the target nucleic acid, which are capable of forming a double stranded RNA region by base-pairing between the regions with sense and antisense nucleotide sequence or by introducing the RNA molecules themselves. Preferably, the RNA molecules comprise simultaneously both sense and antisense nucleotide sequence.

WO 99/61631 relates to methods to alter the expression of a target gene in a plant using sense and antisense RNA fragments of the gene. The sense and antisense RNA fragments are capable of pairing and forming a double-stranded RNA molecule, thereby altering the expression of the gene. This publication also relates to plants, their progeny and seeds derived thereof, obtained using the methods described.

WO 00/49035 discloses a method for silencing the expression of an endogenous gene in a cell, the method involving overexpressing in the cell a nucleic acid molecule of the endogenous gene, wherein the overexpression of the nucleic acid molecule of the endogenous gene and the antisense molecule in the cell silences the expression of the endogenous gene.

SUMMARY AND OBJECTS OF THE INVENTION

The invention provides DNA molecules comprising a plant-expressible promoter operably linked to a DNA region which when transcribed in the cells of a cereal plant yields an RNA molecule comprising a first nucleotide sequence of at least 19 bp having at least 70% nucleotide sequence identity to the sense nucleotide sequence of a BYDV isolate encoding the polymerase gene and a second nucleotide sequence of at least 19 bp having at least 70% nucleotide sequence identity to the complement of the sense nucleotide sequence of an RNA dependent RNA polymerase (hereinafter referred to as "polymerase") gene of a BYDV isolate, such as but not limited to a polymerase comprising the nucleotide sequence of SEQ ID No 1 from the nucleotide at position 1 to the nucleotide at position 1014, and optionally a transcription termination and polyadenylation signal, wherein the first and second nucleotide sequence are capable of forming a double stranded RNA by base pairing between regions which are complementary. The first nucleotide sequence may comprise the nucleotide sequence of SEQ ID No 1 and the second nucleotide sequence may comprise the complement of the nucleotide sequence of SEQ ID No 1. The DNA molecules of the invention may contain a nucleotide sequence encoding a spacer region between the DNA region encoding the first nucleotide sequence and the DNA region encoding the second nucleotide sequence. The spacer region may have the nucleotide sequence of SEQ ID No 2.

The invention also provides a method for producing a cereal plant, such as a cereal plant selected from the group of wheat, barley, rye and oats, e.g. barley, resistant to a Barley Yellow Dwarf Virus comprising the steps of producing a population of transgenic cereal plant lines comprising the DNA molecules of the invention integrated into the genome of the cells of transgenic plant of the plant line and selecting a transgenic cereal plant line resistant to Barley Yellow Dwarf virus infection and optionally comprising the further step of crossing the selected transgenic cereal plant line resistant to Barley Yellow Dwarf virus infection to another cereal plant to obtain progeny plants comprising the DNA molecules of the invention.

Another objective of the invention is to provide a method for producing a cereal plant resistant to a Barley Yellow Dwarf Virus in the presence of a post transcriptional gene silencing inactivating protein, which may be encoded by a co-infecting virus, particularly Cereal Yellow Dwarf Virus, comprising the step of producing a population of transgenic cereal plant lines comprising a DNA molecule of the invention integrated into the genome of the cells of transgenic plant of said plant line and selecting transgenic cereal plant lines resistant to Barley Yellow Dwarf Virus infection.

Yet another objective of the invention is to provide use of a DNA molecule of the invention to produce a transgenic cereal plant resistant to BYDV.

It is also a further objective of the invention to provide the use of a DNA molecule of the invention to produce a transgenic cereal plant resistant to BYDV in the presence of Cereal Yellow Dwarf virus (CYDV).

The invention further provides cereal plants and plant lines, which may be selected from the group consisting of wheat, barley, rye and oat, e.g. barley plant and plant lines comprising stably integrated into the genome of the cells of the cereal plant a DNA molecule according to the invention wherein the cereal plant is resistant to BYDV virus infection and replication of said virus, also in the presence of CYDV.

DETAILED DESCRIPTION OF PREFERRED EMBODIMENTS

Figure 1:
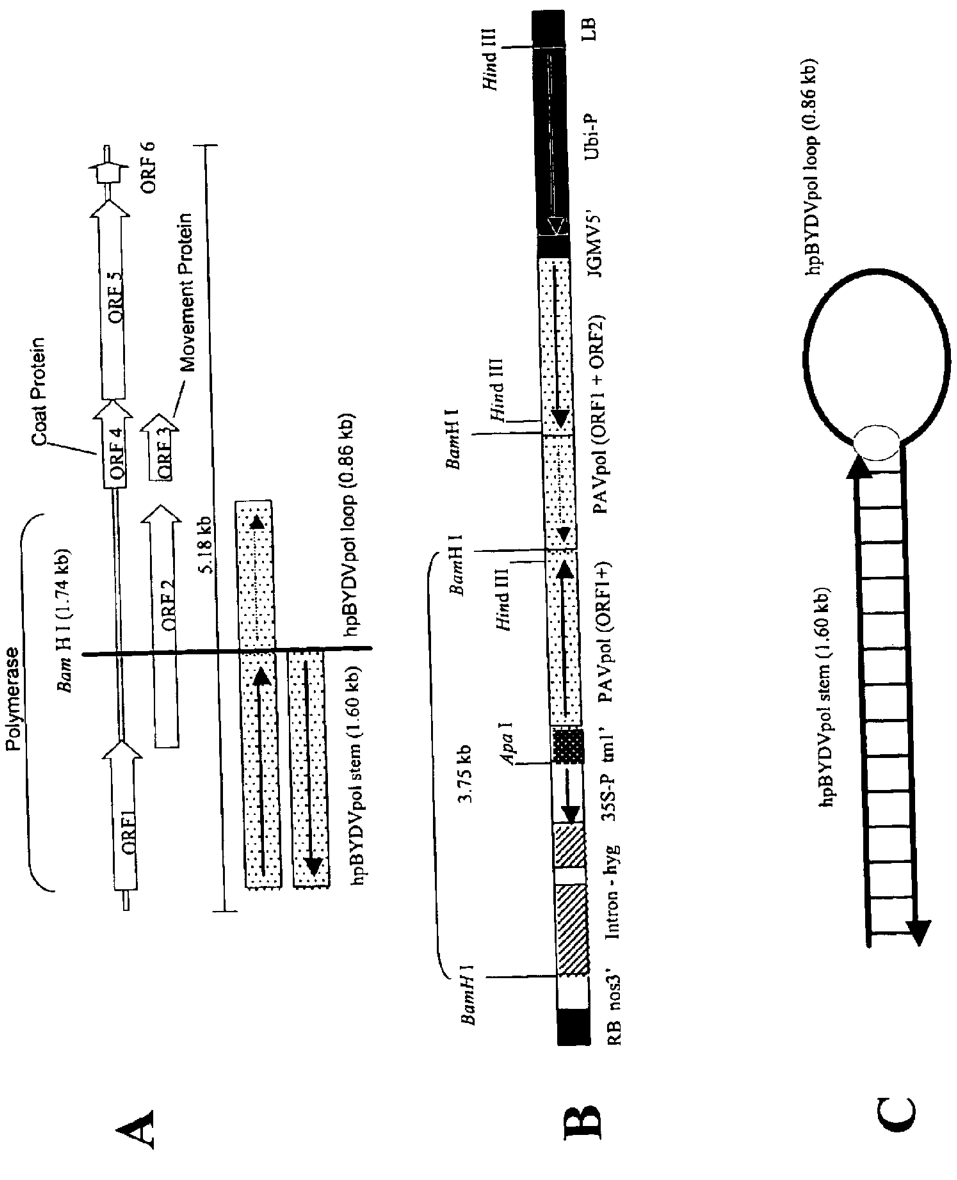
FIG. 1. (A) Genome map of BYDV-PAV showing regions used to generate hpBYDVpol. (B) Design of hpBYDVpol construct. (C) Diagram of self-complementary (hairpin) RNA produced by hpBYDVpol. RB: right border; nos 3': nopaline synthase 3' region; 35S-P: cauliflower mosaic virus 35S promoter; tm1': tumor morphology large gene 3' region; PAVpol: BYDV-PAV polymerase gene sequence; JGMV5': Johnson grass mosaic virus 5' untranslated region; Ubi-P: maize polyubiquitin gene promoter; LB: left border.

Luteoviruses, such as Barley Yellow Dwarf Virus ("BYDV") have been among the most recalcitrant viral group to transgene-mediated resistance (Barker and Waterhouse, 1999). Despite the economic importance of the cereal diseases caused by BYDV, previous attempts to produce transgenic cereals with protection against BYDV have been unsuccessful.

While some attempts (McGrath et al., 1997; Koev et al., 1998) have produced oat or barley plants with resistance (reduced virus replication) or tolerance (reduced virus symptoms but unimpeded virus replication) to BYDV, the inheritance of the resistance/tolerance has been variable. This inheritance has been further complicated by the complex transgene insertion patterns in such plants, especially those obtained using biolistic transformation.

The prior art is thus deficient in providing methods and means for obtaining BYDV resistant cereal plants, with stable inheritance of the resistance gene, using a transgenic approach. The current invention has solved these and other problems as set forth hereinafter in the various embodiments, as well as in the claims.

The current invention is based on the finding that transgenic cereal plants, such as barley, could be made extremely resistant to BYDV infection, replication and disease symptom development using a chimeric gene comprising a promoter which could be expressed in cereal plant cell, and could drive the transcription of an operably linked DNA region, the transcription resulting in an RNA molecule comprising both sense and antisense parts of a BYDV genome corresponding to the nucleotide sequence encoding the RNA dependent RNA polymerase (ORF1). The sense and antisense parts are essentially complementary to each other and thus capable of forming a double stranded RNA. For the virus resistance to occur such a chimeric gene need only to be present as a single transgene, thus resulting in inheritance in a simple Mendelian manner.

In addition, it was realized that the BYDV disease resistance conferred by the chimeric genes according to the invention, could be observed even in the presence of PTGS inactivating protein, such as may be found in the co-infecting Cereal Yellow Dwarf Virus (CYDV-RPV).

Until recently, BYDV was described as having at least six different serotypes, which fell into two different subgroups (Waterhouse et al., 1988; Martin and D'Arcy, 1995). However, comparison of their nucleotide sequences has led to redefining PAV and MAV as species of BYDV, and RPV as a species of *Cereal yellow dwarf virus* (CYDV; Mayo & D'Arcy 1999; Wang et al., 1998). The 3' halves of the two viruses encode movement and coat protein genes and share a fair degree of homology. Their 5' halves encode polymerase gene sequences, which are more closely related to those of other groups of viruses than to each other (Miller et al., 1995; Wang et al., 1998a).

In one embodiment of the invention, a method is provided for producing a cereal plant or plant line resistant to Barley Yellow Dwarf virus infection, virus replication and disease symptom development comprising the steps of a) producing a population of transgenic cereal plant lines comprising a DNA molecule integrated into the genome of the cells of a transgenic plant whereby the DNA molecule comprises the following operably linked elements:
   (1) a plant-expressible promoter;
   (2) a DNA region which when transcribed in the cells of a cereal plant yields a RNA molecule comprising
      (a) a first nucleotide sequence of at least 19 bp having at least 70% nucleotide sequence identity to the sense nucleotide sequence of a BYDV isolate encoding RNA dependent RNA polymerase; and
      (b) a second nucleotide sequence of at least 19 bp having at least 70% nucleotide sequence identity to the complement of said sense nucleotide sequence of a BYDV isolate encoding RNA dependent RNA polymerase; and optionally
      (c) a transcription termination and polyadenylation signal;

wherein the first and second nucleotide sequence are capable of forming a double stranded RNA by base pairing between regions which are complementary; and b) isolating transgenic cereal plants or plant lines resistant to Barley Yellow Dwarf Virus infection.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e. a position in an alignment where a residue is present in one sequence but not in the other is regarded as a position with non-identical residues. The alignment of the two sequences is performed by the Needleman and Wunsch algorithm (Needleman and Wunsch 1970) The computer-assisted sequence alignment above, can be conveniently performed using standard software program such as GAP which is part of the Wisconsin Package Version 10.1 (Genetics Computer Group, Madison, Wis., USA) using the default scoring matrix with a gap creation penalty of 50 and a gap extension penalty of 3.

For the purpose of the invention, the "complement of a nucleotide sequence represented in SEQ ID No: X" is the nucleotide sequence which would be capable of forming a double stranded DNA molecule with the represented nucleotide sequence, and which can be derived from the represented nucleotide sequence by replacing the nucleotides through their complementary nucleotide according to Chargaff's rules (A⇔T; G⇔C) and reading in the 5' to 3' direction, i.e. in opposite direction of the represented nucleotide sequence.

As used herein, nucleotide sequences of RNA molecules may be identified by reference to DNA nucleotide sequences of the sequence listing. However, the person skilled in the art will understand whether RNA or DNA is meant depending on the context. Furthermore, the nucleotide sequence is identical except that the T-base is replaced by uracil (U) in RNA molecules.

The length of the first and second nucleotide sequences may vary from about 10 nucleotides (nt) up to a length equaling the length in nucleotides of part of the BYDV genome encompassing the RNA dependent RNA polymerase encoding ORF of a BYDV genome (normally referred to as ORF 1). The length of the first or second nucleotide sequence may be at least 15 nt, or at least about 20 nt, or at least about 50 nt, or at least about 100 nt, or at least about 150 nt, or at least about 200 nt, or at least about 500 nt, or at least about 1600 bp.

It will be appreciated that the longer the total length of the first nucleotide sequence is, the less stringent the requirements for sequence identity between the total sense nucleotide sequence and the corresponding sequence in the target gene become. The total first nucleotide sequence can have a sequence identity of at least about 75% with the corresponding target sequence, but higher sequence identity can also be used such as at least about 80%, at least about 85%, at least about 90%, at least about 95%, about 100%. The first nucleotide sequence can also be identical to the corresponding part of BYDV genome. However, it is advised that the first nucleotide sequence always includes a sequence of about 19 or 20 consecutive nt, or even of about 50 consecutive nt, or about consecutive 100 nt, or about 150 consecutive nt with 100% sequence identity to the corresponding part of BYDV genome. For calculating the sequence identity and designing the corresponding first nucleotide sequence, the number of gaps should be minimized, particularly for the shorter sense sequences.

The length of the second (antisense) nucleotide sequence is largely determined by the length of the first (sense) nucleotide sequence, and may correspond to the length of the latter sequence. However, it is possible to use an antisense sequence that differs in length by about 10% without any difficulties. Similarly, the nucleotide sequence of the antisense region is largely determined by the nucleotide sequence of the sense region, and may be identical to the complement of the nucleotide sequence of the sense region. Particularly with longer antisense regions, it is however possible to use antisense sequences with lower sequence identity to the complement of the sense nucleotide sequence, such as at least about 75% sequence identity, or least about 80%, or at least about 85%, more particularly with at least about 90% sequence identity, or at least about 95% sequence to the complement of the sense nucleotide sequence. Nevertheless, it is advised that the antisense nucleotide sequences always includes a sequence of about 19 or 20 consecutive nucleotides, although longer stretches of consecutive nucleotides such as about 50 nt, or about 100 nt, or about 150 nt with 100% sequence identity to the complement of a corresponding part of the sense nucleotide sequence may be used. It is clear that the length of the stretch of the consecutive nucleotides with 100% sequence identity to the complement of the sense nucleotide sequence cannot be longer than the sense nucleotide sequence itself. Again, the number of gaps should be minimized, particularly for the shorter antisense sequences. Further, it is also advised that the antisense sequence has between about 75% to 100% sequence identity with the complement of the 5' half of the BYDV genome.

In one embodiment of the invention, the DNA molecules according to the invention may comprise a DNA region encoding a spacer between the DNA region encoding the first and second nucleotide sequences. As indicated in WO 99/53050 the spacer may contain an intron to enhance the BYDV resistance. In one embodiment thereof, the spacer may comprise the nucleotide sequence of SEQ ID No 2.

In another embodiment of the invention, the used DNA molecule has a first and second nucleotide sequence comprising a nucleotide sequence of at least 19 or 20 bp having at least 75% sequence identity to a nucleotide region of a BYDV genome encompassing an ORF comprising the nucleotide sequence of SEQ ID No 1 from the nucleotide at position I to the nucleotide at position 1014, or its complement. It goes without saying that again the sequence identity may be higher, as indicated elsewhere in the specification or the length of the comprised nucleotide sequence may be higher, again as indicated elsewhere in this specification.

In another embodiment of the invention, the first nucleotide sequence comprises the nucleotide sequence of SEQ ID No 1 and the second nucleotide sequence comprises the nucleotide sequence of the complement of SEQ ID No 1.

However, the nucleotide sequence of the complete genome of a number of BYDV isolates is known and available through databases such as, e.g., Genbank, and the person skilled in the art can easily identify the nucleotide sequences corresponding to the sequence of SEQ ID No 1 in those nucleotide sequences. These nucleotide sequences derived from other BYDV isolates can be used to generate BYDV resistant cereal plants and plant lines to equal effect.

The following nucleotide sequences of complete genomes of BYDV isolates are available: Genbank accession Nr NC_002160/GI:9634102; Genbank accession Nr NC_001599/GI:9627413; Genbank accession Nr AF235167/GI:7417288; Genbank accession Nr AF218798/GI:6715477; Genbank Accession Nr D85783/GI:1395150; GenbankAccession Nr D11032/GI:221098; GenbankAccession Nr D10206/GI:221091; Genbank Accession Nr D11028/GI:221084; Genbank Accession Nr X07653/GI:58798; Genbank Accession Nr L25299/GI:408929.

Sequences corresponding to the nucleotide sequence used to exemplify the current invention may be identified in other BYDV genomes e.g. by using computer-assisted alignment programs. Alternatively, the sequences can be identified and isolated using PCR and the oligonucleotide primer with nucleotide sequences as in SEQ ID 3 and 4, essentially similar nucleotide sequences (having at least 85% sequence identity, or at least 90% sequence identity).

It will be clear that also nucleotide molecules hybridizing under stringent conditions to a nucleotide comprising the sequence of SEQ ID No 1 or similar corresponding sequences from other BYDV genomes may also be used to similar effect.

"Stringent hybridization conditions" as used herein mean that hybridization will generally occur if there is at least 95% and preferably at least 97% sequence identity between the probe and the target sequence. Examples of stringent hybridization conditions are overnight incubation in a solution comprising 50% formamide, 5× SSC (150 mM NaCl, 15 mM trisodium citrate), 50 mM sodium phosphate (pH 7.6), 5× Denhardt's solution, 10% dextran sulfate, and 20 $\mu$g/ml denatured, sheared carrier DNA such as salmon sperm DNA, followed by washing the hybridization support in 0.1× SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

The invention is also directed to a method of protecting a cereal plant against BYDV virus in the presence of a PTGS inactivating protein. Such proteins and nucleotide regions encoding them have been identified in several viruses and endogenous orthologous genes in plants have been identified. As used herein, a PTGS inactivating protein is a protein, which when present in a plant cell results in a reduction of the post transcriptional gene silencing observed when sense or antisense RNA molecules are present in that cell.

In one embodiment, the PTGS inactivating protein is encoded by a virus, such as Cereal Yellow Dwarf Virus. The methods of the invention therefor can also be used to produce cereal plants resistant to Barley Yellow Dwarf Virus, and Cereal Yellow Dwarf Virus co-infection.

It goes without saying that the DNA molecules for use in the invention may comprise a first nucleotide sequence comprising several different sense nucleotide sequences corresponding to parts of a BYDV genome (as hereinbefore described) and a second nucleotide sequence comprising the several corresponding complementary nucleotide sequences of the several different sense nucleotide sequences in the first nucleotide sequence. Moreover, a single DNA molecule for use in the invention may comprise within its first nucleotide sequence simultaneously several different sense nucleotide sequences corresponding to parts of a BYDV genome as well as different sense nucleotide sequences corresponding to parts of another viral genome such as a CYDV genome.

Thus the invention also provides a method for protecting cereal plants, such as but not limited to barley plants, against a BYDV and CYDV co-infection, the method comprising a) producing a population of transgenic cereal plant lines comprising a DNA molecule, wherein the DNA molecule comprises the following operably linked DNA elements
  i) a plant-expressible promoter;
  ii) a DNA region which when transcribed in the cells of a cereal plant yields an RNA molecule comprising
    1) a first nucleotide sequence comprising a multitude of nucleotide sequences, each comprising at least 19 or 20 bp having at least 70% nucleotide sequence identity to the sense nucleotide sequence of a BYDV isolate or a CYDV isolate
    2) a second nucleotide sequence having at least 70% nucleotide sequence identity to the complement of the first nucleotide sequence; and
  iii) a transcription termination and polyadenylation signal; wherein the first and second nucleotide sequence are capable of forming a double stranded RNA by basepairing between the regions which are complementary; and
b) isolating transgenic cereal plant lines resistant to Barley Yellow Dwarf Virus and Cereal Yellow Dwarf Virus infection.

In one embodiment of the above mentioned method, the first nucleotide sequence comprises the nucleotide sequence of SEQ ID No 7 from the nucleotide at position 429 to the nucleotide at position 629 (corresponding to ORF1 of BYDV Australian isolate with the genomic sequence available under Genbank Accession number X 07653) and the nucleotide sequence of SEQ ID No 7 from the nucleotide at position 2314 to the nucleotide at position 2514 (corresponding to ORF2 of an Australian BYDV isolate) and the nucleotide sequence of SEQ ID No 7 from the nucleotide at position 5052 to the nucleotide at position 5270 (ORF6+3' untranslated end of BYDV) and the nucleotide sequence of SEQ ID No 8 and the nucleotide sequence of SEQ ID No 9 (the latter two sequences corresponding to part of a CYDV genome) and the second nucleotide sequence comprises the about exact complement of the first nucleotide sequence.

The invention also extends to DNA molecules for use to produce BYDV resistant cereal plants described herein as well as plant cells and cereal plants comprising a DNA molecule according to the invention.

The DNA molecules of the invention suitable for the production of BYDV or BYDV/CYDV resistant plants may be introduced into cereal plant lines, already comprising the natural BYDV resistance alleles such as the mentioned Yd2 or Bdv1 genes to obtain an additive or synergistic effect on virus resistance.

The method and means of the invention are suited for cereal crop plants such as wheat, rye, oat and barley, but may also be used for protecting other grasses and small grain cereals susceptible to BYDV or closely related viruses.

It will be clear that actual method of transforming the cereal crop has little importance for the current method and several methods including Agrobacterium mediated transformation, microprojectile bombardment, electroporation of compact embryogenic calli, silicon whisker mediated DNA introduction are available in the art.

The obtained transformed plant can be used in a conventional breeding scheme to produce more transformed plants with the same characteristics or to introduce the DNA molecule for obtaining BYDV resistance according to the invention in other varieties of the same or related plant species, or in hybrid plants. Seeds obtained from the transformed plants contain the chimeric genes of the invention as a stable genomic insert and are also encompassed by the invention.

The following non-limiting Examples describe the construction of DNA molecules suitable for use in making BYDV resistant cereal plant lines. Unless stated otherwise in the Examples, all recombinant DNA techniques are carried out according to standard protocols as described in Sambrook and Russell (2001) *Molecular Cloning: A Laboratory Manual*, Third Edition, Cold Spring Harbor Laboratory Press, NY, in Volumes 1 and 2 of Ausubel et al. (1994) *Current Protocols in Molecular Biology, Current Protocols*, USA and in Volumes I and II of Brown (1998) *Molecular Biology LabFax*, Second Edition, Academic Press (UK). Standard materials and methods for plant molecular work are described in *Plant Molecular Biology Labfax* (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) *PCR Primer: A Laboratory Manual*, Cold Spring Harbor Laboratory Press, and in McPherson at al. (2000) PCR-*Basics: From Background to Bench*, First Edition, Springer Verlag, Germany.

All the nucleotide sequences identified in this text by their database accession number are hereby incorporated by reference.

Throughout the description and Examples, reference is made to the following sequences:

SEQ ID No 1: part of the Barley Yellow Dwarf Virus genome spanning ORF1 and 5' end of ORF2.

SEQ ID No 2: part of the Barley Yellow Dwarf Virus genome spanning the 3' end of ORF2.

SEQ ID No 3: PCR oligonucleotide primer 1

SEQ ID No 4: PCR oligonucleotide primer 2

SEQ ID No 5: PCR oligonucleotide primer 3

SEQ ID No 6: PCR oligonucleotide primer 4

SEQ ID No 7: nucleotide sequence of an Australian isolate of BYDV (Genbank accession X07653)

SEQ ID No 8: nucleotide sequence of part of an Australian isolate of CYDV (from Genbank accession AF 020090)

SEQ ID No 9: nucleotide sequence of part of an Australian isolate of CYDV (from Genbank accession AF 020090)

EXAMPLES

Experimental Procedures

Barley Transformation

*Hordeum vulgare* L. cv. 'Golden Promise' was transformed with the hpBYDVpol construct using the Agrobacterium inoculation procedure and target tissue as described by Tingay et al. (1997). Freshly dissected scutella (with embryo axes removed) were immersed for 10 min in a suspension of *Agrobacterium tumefaciens* AGL1:hpBYDVpol or AGL0:hpBYDVpol, that was obtained by inoculating 5 mL of antibiotic-free MG/L medium (Tingay et al., 1997) with 250 $\mu$L of overnight Agrobacterium culture (grown in the presence of 50 mg/L spectinomycin and 25 mg/L rifamipicin) with shaking at 28° C. The scutella were blotted briefly with sterile filter paper to remove excessive liquid, placed with the smooth side down on solid callus induction medium, and incubated at 25° C. for 2–3 days. The scutella were then transferred without washing to callus induction medium containing 30 mg/L hygromycin and 150 mg/L Timentin™, again with the smooth side down. They were subcultured twice, at two weeks intervals, on callus induction medium containing 50 mg/L hygromycin and 150 mg/L Timentin™ to produce hygromycin-resistant calli, which were subsequently transferred to regeneration medium containing 25 mg/L hygromycin, and 150 mg/L Timentin™. Callus pieces forming shoots on the regeneration medium were transferred either directly to rooting medium containing 25 mg/L hygromycin or first to a half-strength regeneration medium and then to rooting medium.

Testing Transgenic Plants for BYDV Resistance

Unless stated otherwise, aphids (*Rhopalosiphum padi*) were allowed to feed for 48 hr on virus-infected oat leaves then transferred (5–10 per plant) onto ten-day-old test plants. The virus isolates used were an Australian isolate of BYDV-PAV, an Australian isolate of CYDV-RPV and an Australian B/CYDV-MIX isolate which contained both BYDV-PAV and CYDV-RPV (Waterhouse et al., 1986). After a 72 hr inoculation feeding period on the test plants, the aphids were killed with pyrethrin and the plants transferred to a glasshouse (16 hr day 18° C.; 8 hr night 13° C.). Virion accumulation was measured, unless stated otherwise, 21 and 28 days after inoculation, by enzyme-linked immunosorbent assay (ELISA) (Xin et al., 1988), using monoclonal antibody diagnostic kits for BYDV-PAV and CYDV-RPV supplied by Sanofi Pasteur Diagnostics. The conversion of substrate was measured after four hours incubation.

Analysis of Transgenic Plants by DNA Hybridization

Genomic DNA was isolated from barley leaves using the procedure of Lagudah et al. (1991). Approximately 10 $\mu$g DNA was digested overnight with Hind III, Apa I or BamHI and electrophoresed in a 1% agarose gel (Sambrook et al., 1989). The DNA was blotted onto Hybond™-N+ positively charged nylon membrane using 20× SSC, in accordance with the procedure supplied by Amersham Life Science. Hybridization was conducted at 42° C. in a formamide buffer using a radiolabeled probe from a 1.1 KB hpt (hygromycin resistance gene) fragment. The hybridized membranes were washed as recommended in the Amersham protocol and analyzed using a PhosphorImager (Molecular Dynamics).

Analysis of Transgenic Plants by PCR

Genomic DNA for PCR template was prepared as for Southern analysis. Oligonucleotide primers (5'-TGTGGCAGTGGAGAGMGAG-3' (SEQ ID No 5) and 5'-ATGTTGTTGGTGATTTGGTG-3' (SEQ ID No 6) were used to identify T1 progeny containing the hpBYDVpol gene. These primers amplify a 626 nt fragment from ORF2 of BYDV. The amplified region forms part of the spacer loop between sense and antisense sequences of the hpBYDVpol gene. PCR analysis was performed using AmpliTaq Gold™ according to manufacturers instructions using approximately 100 ng of genomic DNA. PCR reactions were performed in a thermal sequencer (FTS 960, Corbett research); 94° C. 12 min; 5 cycles 94° C. 1 min, 60° C. 2 min, 72° C. 3 min; 25 cycles 94° C. 30 sec, 60° C. 2 min, 72° C. 1 min 30 sec; 70° C. 1 min. Electrophoretic analysis of PCR products was conducted using 1% agarose gels buffered in 1× TBE.

Example 1

Construction of the Hairpin Gene (hpBYDVpol)

A full-length BYDV-polymerase (BYDVpol) sequence was amplified from a cDNA clone of an Australian BYDV-PAV isolate (GenBank Accession No. D11032) using GeneAmp XL PCR kit (Perkin Elmer), with a pair of primers (5'-ACCATTCTATTGTGCTCTCGCACA-GAGATAAGCAGGAAACC ATGGTTTTCGAAATACTMTAGGT-3' (SEQ ID No 3) and 5'-CCGGAATTCTTAATATTCGTTTTGTGAG-3' (SEQ ID No 4) that introduced a Nco I site and an EcoR I site at the 5' end and the 3' end, respectively. The underlined nucleotides are from the BYDV-PAV sequence. The resulting PCR fragment was digested with Nco I and EcoR I, and cloned into pUJJT (Wang and Waterhouse, 2000) at the corresponding sites, forming the Ubi1-JGMV5'-BYDVpol-tm1' cassette. A 1.6 kb sequence from the 5' half of BYDVpol was excised with Nco I and BamH I from the PCR fragment, treated with Klenow polymerase to generate blunt ends, and inserted into the EcoR I site (also pre-treated with Klenow) between BYDVpol and tm1' in the Ubi1-JGMV5'-BYDVpol-tm1' cassette, giving the hairpin gene hpBYDVpol (FIG. 1). For barley transformation, the hairpin gene cassette was excised with Not I and inserted into pWBVec8, which contains an intron-interrupted hygromycin resistance gene, as the selectable marker, in the T-DNA region (Wang et al., 1998b).

Example 2

Transformation and Analysis of $T_0$ Plants

A gene construct (hpBYDVpol) was made in which a hairpin RNA, containing BYDV-PAV polymerase gene sequences, is transcribed under the control of the maize ubiquitin promoter (FIG. 1). Using this construct and an Agrobacterium-mediated transformation system, an overall transformation efficiency of 13% was achieved resulting in 38 independent transgenic barley plants (Table 1).

TABLE 1

Transformation of barley with hpBYDVpol.

| Strain of Agrobacterium | Acetosyringone conc. in co-cultivation medium ($\mu$M) | No. scutella used | No. hygromycin resistant calli generated | No. transgenic lines generated |
|---|---|---|---|---|
| AGL0 | 0 | 72 | 40 (55%)[A] | 17 (24%) |
| | 200 | 70 | 40 (57%) | 8 (11%) |
| AGL1 | 0 | 71 | 17 (24%) | 6 (8%) |
| | 200 | 72 | 22 (30%) | 7 (10%) |

[A]Numbers in brackets = No. transgenic calli or plants/No. scutella (as a percentage)

Figure 2:
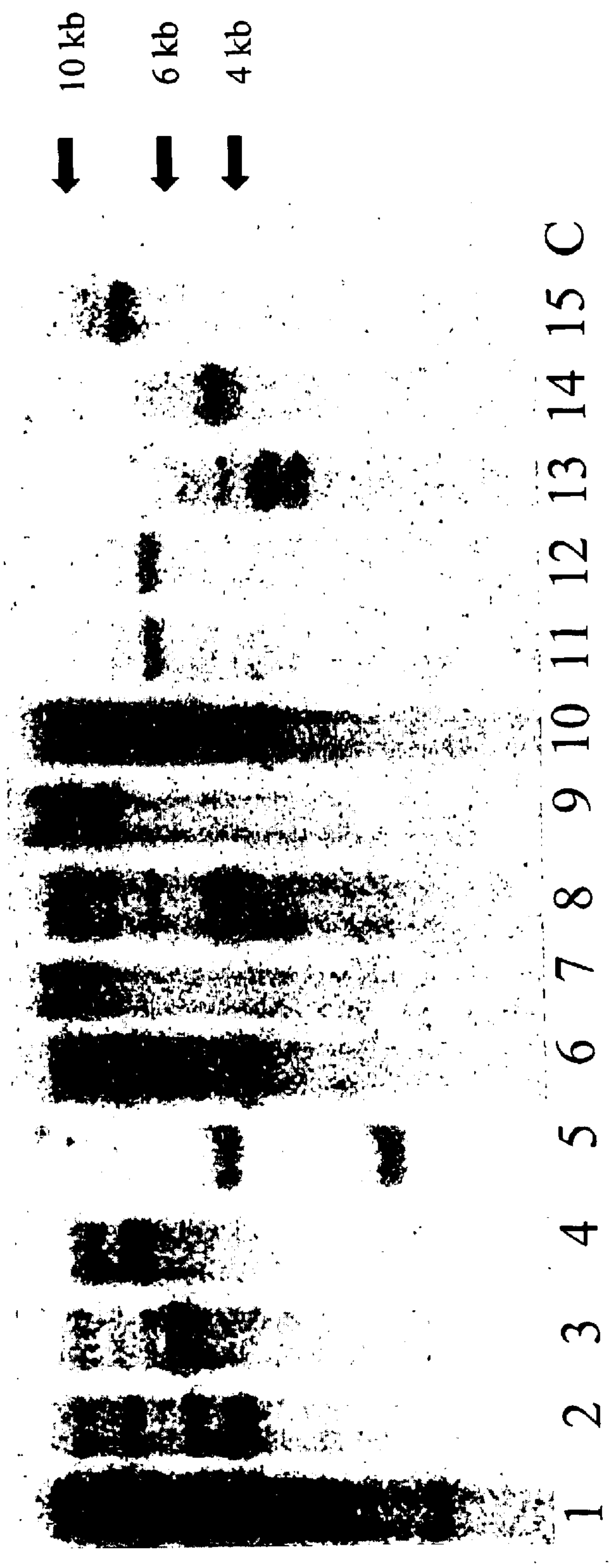
FIG. 2. Southern blot analysis of 15 primary $T_0$ hpBYDVpol barley transformants. DNA was digested with Hind III, separated by electrophoresis, blotted to Hybond N+™ membrane and hybridized with a radioactively labeled hpt probe. The number of intense bands in each in each lane should represent the number of transgene copies in the plant line. Weak bands may be due to partial digestion of DNA.

Southern analysis indicated that 19 plants carried a single transgene copy, 12 contained two copies and 7 had three or more copies. The analysis of the first 15 of these plants is shown in FIG. 2. When 25 of the $T_0$ plants were inoculated with BYDV-PAV, 9 of them appeared highly resistant as they supported little or no virus replication when measured by ELISA (data not shown). Six lines (1–6) were selected for further analysis; four of these appeared highly resistant and two appeared susceptible to BYDV-PAV infection (Table 2).

TABLE 2

Testing $T_0$ and $T_1$ hpBYDVpol plants for virus resistance.

| $T_0$ Line number | $T_0$ Reaction to BYDV-PAV | $T_0$ Number of transgene copies (Southern) | $T_1$ Segregation Highly resistant: Susceptible (ELISA) |
|---|---|---|---|
| 1 | Highly resistant | >5 | 1:2 |
| 2 | Highly resistant | 1 | 18:12[A] |
| 3 | Susceptible | 1 | 0:15 |
| 4 | Highly resistant | 1 | 17:10[A] |
| 5 | Highly resistant | 2 | 15:2[B] |
| 6 | Susceptible | >5 | 0:30 |

[A]The segregation for BYDV resistance versus susceptibility conforms to a 3:1 ratio for a single dominant locus (Chi-square test, $p > 0.05$).
[B]The segregation for BYDV resistance versus susceptibility conforms to a 15:1 ratio for two dominant loci (Chi-square test, $p > 0.05$).

Example 3

Analysis of $T_1$ Plants for Response to BYDV-PAV Inoculation

About 20 seed from each of the 6 $T_0$ Lines were sown in soil. The resulting plants were inoculated with BYDV-PAV and assayed by ELISA three weeks later (Table 3).

hpBYDVpol transgene was conferring extreme resistance to BYDV-PAV in four of the six transgenic barley lines analyzed and, in three of them (Lines 2, 4 and 5), this was inherited in a predictable Mendelian manner.

Figure 4:
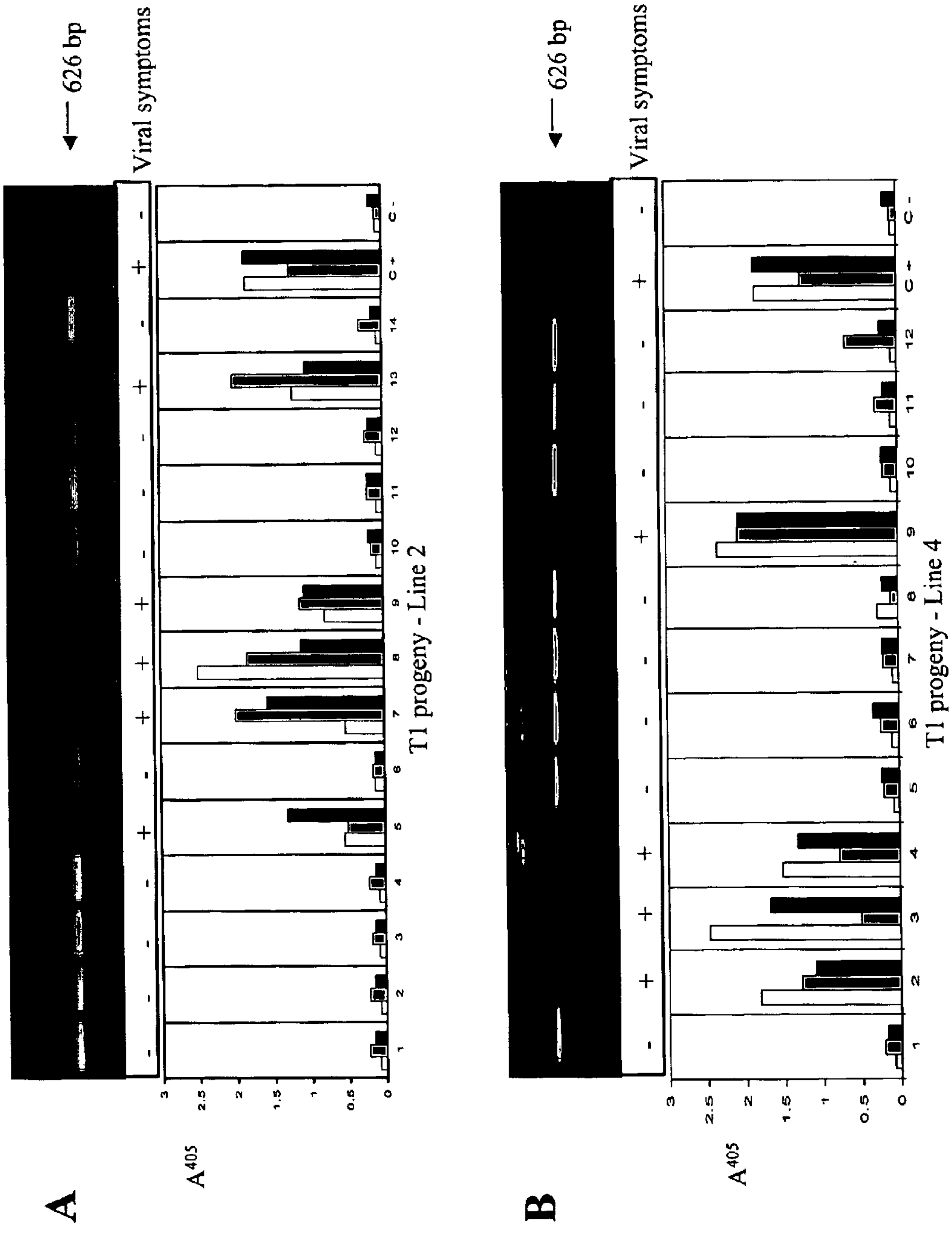
FIG. 4. Relationship between virion accumulation and inheritance of the hpBYDVpol transgene. Virus levels detected by ELISA 21 (white bar), 28 (gray bar) and 42 (black bar) days after inoculation in (A) 14 $T_1$ progeny of Line 2 and (B) 12 $T_1$ progeny of Line 4. Displayed above each histogram is a symbol representing the severity of viral symptoms in mature plants and an agarose gel containing PCR products from the corresponding plant samples; the presence of a 626 bp product indicates the amplification and detection of the hpBYDVpol transgene.

Transgene inheritance and virus immunity in hpBYDVpol Lines 2 and 4 Inheritance of the hpBYDVpol transgene and of BYDV-PAV resistance was further examined in Lines 2 and 4. Fourteen $T_1$ plants of each line were challenged with BYDV-PAV and monitored for virus symptoms and virion accumulation 21, 28, and 42 days after inoculation. The inheritance of the hpBYDVpol transgene in these plants was examined by PCR amplification of a 626 bp fragment of DNA from the transgene. In both lines (FIG. 4), the inheritance of hpBYDVpol correlated perfectly with lack of virus symptoms and resistance to BYDV infection. Plants that were symptomless and contained undetectable virus levels 21 days after inoculation and remained this way throughout the six weeks of analysis (FIG. 5A), whereas those plants without the hpBYDVpol transgene showed virus symptoms and virion accumulation at all three time-points. The co-segregation of virus accumulation with the absence of the transgene was also evident in the grain yield from the individual progeny plants. In Line 2, the average grain yield from the nine hpBYDVpol-containing T1 progeny was 29.7±1.8 g compared to a yield of 20.9±1.5 g from the six transgene-free progeny. Twenty-eight days after inoculation, the ELISA level in plant 12 of Line 4 (FIG. 4) suggested that some virus accumulation had occurred. However, the plant had undetectable levels of BYDV-PAV both one week before and two weeks after this time-point, and never developed virus symptoms. This suggests that there might have been a low level of virus replication, peaking at 28 days, which was

TABLE 3

Virus level, measured by ELISA, for groupings of highly resistant and susceptible T1 progeny of transgenic Lines 2 and 4, following inoculation with either BYDV-PAV or CYDV-RPV.

| Challenge virus | BYDV-PAV | | CYDV-RPV | |
|---|---|---|---|---|
| Reaction to infection | Highly resistant | Susceptible | Highly resistant | Susceptible |
| Line 2 | 0.103 ± 0.001[A] (9)[B] | 1.148 ± 0.074 (6) | −(0) | 1.136 ± 0.061 (15) |
| Line 4 | 0.109 ± 0.036 (9) | 1.741 ± 0.075 (3) | −(0) | 1.373 ± 0.107 (15) |
| Control + | 1.040 ± 0.172 (5) | | 1.070 ± 0.102 (6) | |
| Control − | 0.105 ± 0.003 (6) | | 0.147 ± 0.003 (6) | |

Figure 3:
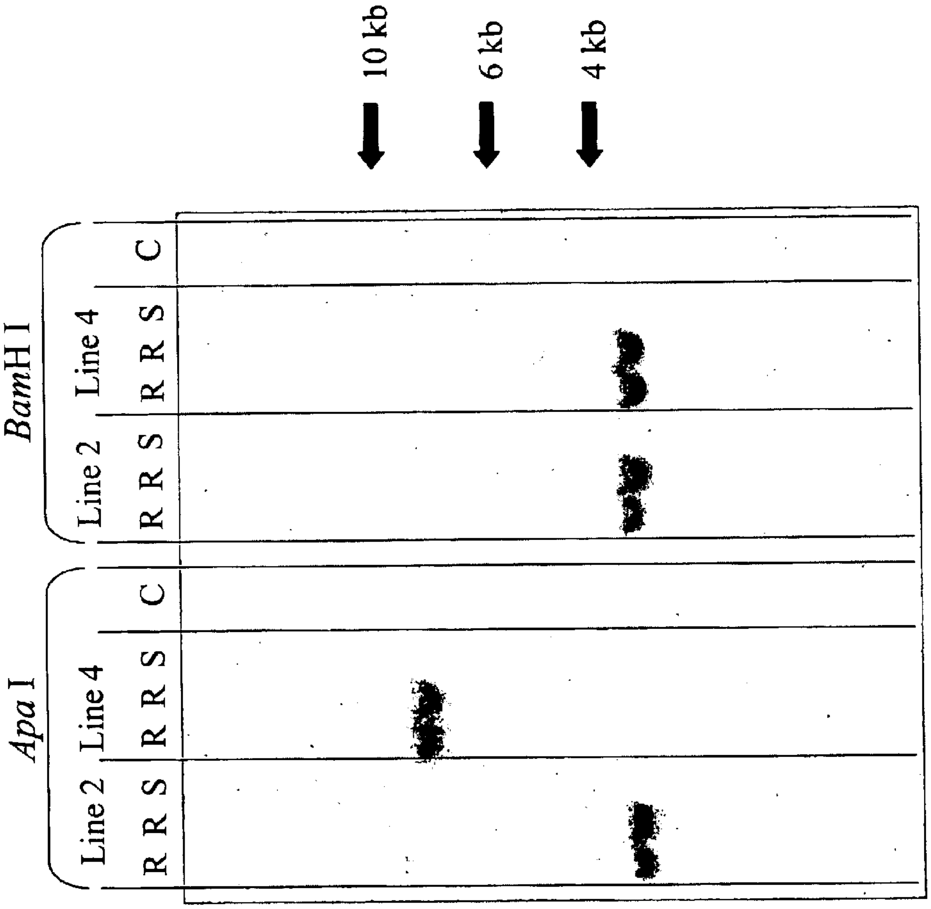
FIG. 3. Southern blot analysis of T1 progeny of hpBYDVpol Lines 2 and 4. DNA from two resistant (R) and one susceptible (S) T1 plants for Lines 2 and 4, and for non-transgenic barley (C), was digested with Apa I or BamH I, separated by electrophoresis, blotted to Hybond N+™ membrane and hybridized with a radioactively-labeled hpt probe. The number of bands in the Apa I lanes and the intensity of the 3.75 KB bands for the BamH I lanes should indicate copy number.

[A]ELISA reading (with Standard Errors) of plants, 28 days post inoculation
[B]Numbers of plants are shown in brackets
Control + = challenged wildtype plants; Control − = unchallenged wildtype plants All of the plants from Lines 3 and 6 were as susceptible to BYDV-PAV infection as their $T_0$ parents had been, whereas the progeny of each of the other lines (which were all resistant as $T_0$ plants) contained some plants that were susceptible and others that were resistant. The $T_0$ Line 1 plant produced a total of eighteen seed and of these only three germinated. One of the three plants that grew was found to be resistant to BYDV, while the other two were susceptible. The progeny of Lines 2 and 4 conformed to a segregation ratio of 3:1 (highly resistant: susceptible), suggesting the presence of a single dominant transgene locus in each line and Southern analysis (FIG. 3) revealed that the loci each appear to contain a single transgene. Plants from Line 5 conformed most closely to a segregation ratio of 15:1 (highly resistant: susceptible), implying the presence of two dominant loci. Taken together, the results suggested that the then overcome by the transgene-induced resistance or that there was some contamination of the sample during analysis.

Specificity and Robustness of the Virus Resistance

Figure 5:
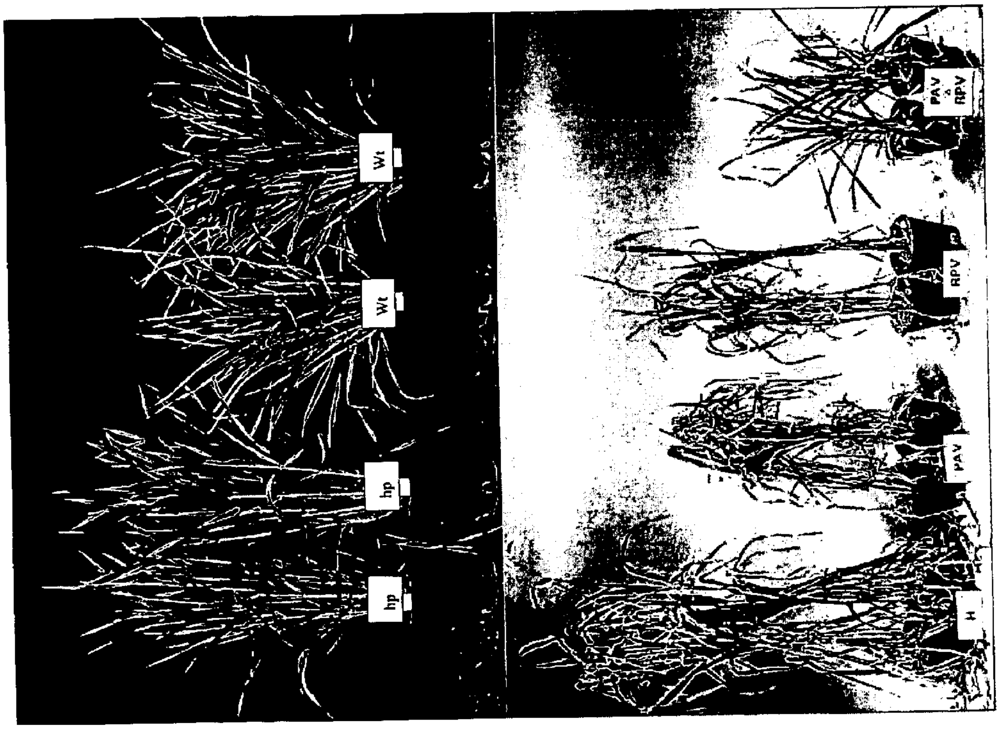
FIG. 5. Reaction of transgenic barley, non-transgenic barley, and oats to BYDV and CYDV. A. Reaction of transgenic, and non-transgenic barley plants to BYDV-PAV. Two T1 hpBYDVpol resistant plants of Line 2 (left) and two non-transformed barley plants (right). B. Coast-black oats (Avena sativa) infected with BYDV-PAV, CYDV-RPV and B/CYDV-MIX, a mixture of both isolates.

Although BYDV-PAV is the major virus pathogen of cereals in the field, CYDV-RPV can also be present. Indeed the two viruses can occur as a complex and appear to have a synergystic effect on symptom severity (FIG. 5B). The viruses share common hosts, a common insect vector and many aspects of their biology. However, they are at opposite ends of the luteovirus spectrum in terms of sequence homology and genome organization. To test whether the hpBYDVpol transgene also conferred protection against CYDV-RPV, approximately 15 $T_1$ progeny from each of hpBYDVpol Lines 2 and 4 were challenged with BYDV-PAV and another 15 of each line with CYDV-RPV. Measuring the virus accumulation in these plants by ELISA revealed that, as before, both lines segregated 3:1 for BYDV-PAV resistance. However, all of the plants inoculated with CYDV-RPV were fully susceptible to the virus (Table 3). These results indicate that the resistance conferred by the hpBYDVpol transgene is specific to BYDV-PAV. This might have been expected, as there is only 34% homology between nucleotide sequence in hpBYDVpol and the corresponding region in CYDV-RPV.

Some viruses have the capacity to enhance the replication and/or spread of co-infecting viruses and to inactivate PTGS (Vance 1991; Vance et al., 1995; Pruss et al., 1997; Shi et al., 1997; Voinnet et al, 1999). Therefore, it was possible that infection by CYDV-RPV, which can co-infect with BYDV-PAV in the field, could enhance the replication and spread of BYDV-PAV or inactivate the hpBYDVpol-mediated BYDV-PAV immunity, thus disarming the plant's newly conferred protection. It has recently been shown that some viruses have the capacity to inactivate PTGS (Voinnet et al. 1999). The P1 protein of the Sobemovirus, *Rice yellow mottle virus*, inactivates PTGS (Voinnet et al., 1999). Its gene may be orthologous to ORF1 (and possibly parts of ORF2) of CYDV-RPV.

Figure 6:
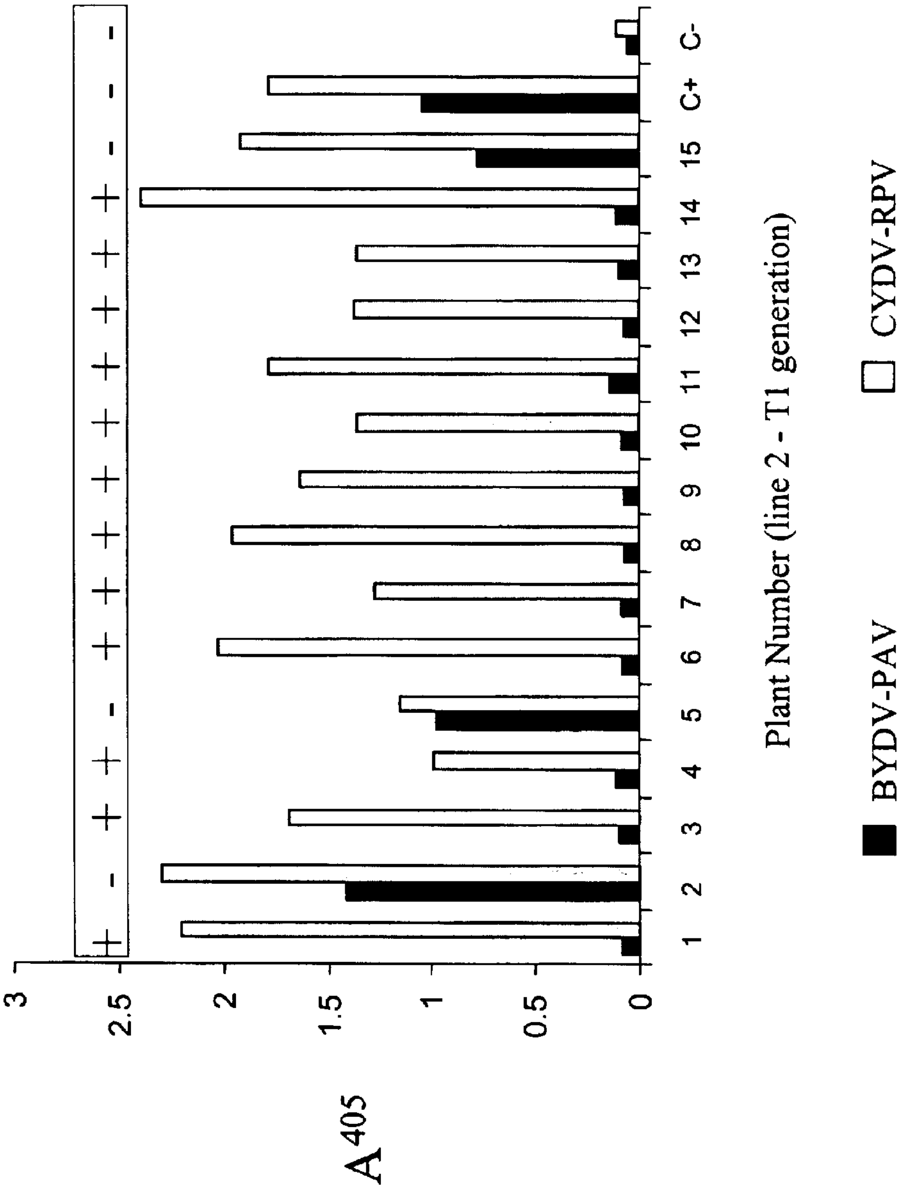
FIG. 6. BYDV-PAV and CYDV-RPV accumulation in a population of segregating progeny from hpBYDVpol Line 2. Virus levels, detected by strain-specific ELISA, 21 days after inoculation, in 15 progeny plants inoculated with B/CYDV-MIX (a complex of both BYDV-PAV and CYDV- RPV). The pair of dark and light histogram bars for each progeny plant represent the levels of BYDV-PAV and CYDV-RPV detected, respectively. The + and – above each pair indicate whether or not the plant has inherited the hpBYDVpol transgene. The transgene status was determined by PCR as in FIG. 3. C+ and C– are results for non-transgenic control plants that have been challenged and not challenged with B/CYDV-MIX, respectively.

Therefore, it was important to determine whether infection by CYDV-RPV could inactivate the hpBYDVpol-mediated BYDV-PAV resistance. To test this, 15 $T_1$ progeny from hpBYDVpol Line 4 were inoculated with the B/CYDV-MIX isolate, a virus complex containing BYDV-PAV and CYDV-RPV. The plants were subsequently tested using species-specific ELISA for accumulation of BYDV-PAV and CYDV-RPV and by PCR for inheritance of the transgene. The results (FIG. 6) showed that CYDV-RPV replicated to high levels in all 15 plants but that the 12 plants inheriting the hpBYDVpol transgene were resistant to BYDV-PAV.

This shows that the resistance to PAV is not compromised by replication of CYDV-RPV and further confirms the 3:1 (BYDV-PAV resistance: susceptible) segregation ratio.

Recovery of Virus from Virus-Challenged hpBYDVpol Plants

Although BYDV-PAV-challenged hpBYDVpol-plants contain extremely low levels of BYDV-PAV antigen, they might contain sufficient virus to be acquired by aphids and thus be of ecological significance. To examine this, we attempted to recover infectious virus from T1 progeny plants from lines 2 and 4 that had been previously challenged with either BYDV-PAV or B/CYDV-MIX. Virus-free aphids were fed (for three days) on the plants ten weeks after the initial challenge and then transferred to healthy test plants (Table 4).

TABLE 4

Recovery of virus from transgenic and non-trausgenic barley plants inoculated with BYDV-PAV or B/CYDV-MIX.

| Challenge virus | Genotype[A] | Recovery of BYDV-PAV[B] | Recovery of CYDV-RPV[B] |
|---|---|---|---|
| BYDV-PAV | Line 2 + t | 0/4 (0.084 ± 0.004)[C] | — |
| | Line 2 − t | 1/1 (2.069) | — |
| | Line 4 + t | 0/4 (0.076 ± 0.003) | — |
| | Line 4 − t | 1/1 (1.185) | — |
| | Control | 3/3 (1.212 ± 0.081) | — |
| B/CYDV-MIX (BYDV-PAV and CYDV-RPV) | Line 2 + t | 0/4 (0.069 ± 0.004) | 4/4 (0.895 ± 0.174) |
| | Line 2 − t | 1/1 (1.191) | 1/1 (0.819) |
| | Line 4 + t | 0/4 (0.094 ± 0.025) | 4/4 (1.576 ± 0.134) |
| | Line 4 − t | 1/1 (0.954) | 1/1 (0.909) |
| | Control | 3/3 (1.108 ± 0.166) | 3/3 (1.473 ± 0.300) |

TABLE 4-continued

[A]+ t = segregant containing the hpBYDVpol transgene; −t = segregant without hpBYDVpol
[B]Number of test plants infected/Number inoculated
[C]Numbers in brackets are average ELISA readings and associated Standard Errors Whereas the test plants became infected with BYDV-PAV from aphids fed on BYDV-PAV or B/CYDV-MIX challenged wildtype or non-transgene segregant plants, none of them was infected with BYDV-PAV from aphids fed on similarly challenged plants containing the hpBYDV-PAVpol transgene. However, aphids did recover CYDV-RPV from hpBYDVpol plants challenged with the B/CYDV-MIX mixture. Taken altogether, the data show that BYDV-PAV-challenged hpBYDVpol plants contain no biologically active virus and should be regarded as immune to BYDV-PAV.

Example 4

Construction of a DNA Construct Encoding dsRNA with Multiple Target Regions in the BYDV and CYDV Genomes Using conventional recombinant DNA techniques, the following chimeric genes are constructed comprising the following operably linked DNA elements:

a maize ubiquitin promoter region (Christensen and Quail, 1996) or subterranean clover stunt virus promoter S4 region or subterranean clover stunt virus promoter S7 region comprising an Adh1 intron (WO 9606932) a first nucleotide sequence comprising in order

- a. the nucleotide sequence of SEQ ID No 7 from nucleotide 2314 to nucleotide 2514;
- b. the nucleotide sequence of SEQ ID No 7 from nucleotide 429 to nucleotide 629;
- C. the nucleotide sequence of SEQ ID No 7 from nucleotide 5052 to nucleotide 5270;
- d. the nucleotide sequence of SEQ ID No 8; and
- e. the nucleotide sequence of SEQ ID No 9;

a second nucleotide sequence which comprise the complement of the first nucleotide sequence a transcription termination and polyadenylation signal The DNA molecule is introduced into barley plants, and BYDV/CYDV resistant barley plant lines are isolated.

REFERENCES

1) Barker, H. and Waterhouse, P. M. (1999) The development of resistance to Luteoviruses mediated by host genes and pathogen-derived transgenes. In: The Luteoviridae. (Smith, H. G. and Barker, H., eds) CABI publishing, Wallingford, UK, pp. 169–210.

2) Burnett, P. A., Comeau, A. and Qualset, C. O. (1995) Host plant tolerance or resistance for control of barley yellow dwarf. In: Barley yellow dwarf: 40 years of progress. (D'Arcy, C. J. and Burnett, P. A., eds) APS press, St Paul, Minn., pp. 321–343.

3) Hamilton, A. J. and Baulcombe D. C. (1999) A species of small antisense RNA in posttranscriptional gene silencing in plants. Science 286, 950–952.

4) Kawchuck, L. M., Lynch, D. R., Martin, R. R., Kozub, G. C. and Farries, B. (1997) Field resistance to the potato leafroll luteovirus in transgenic and somaclone potato plants reduces tuber disease symptoms. *Can. J. Plant Pathol.* 19, 260–266.

5) Koev, G, Mohan, B. R., Dinesh-Kumar, S. P., Torbert, K. A., Somers, D. A. and Miller, W. A. (1998) Extreme reduction of disease in oats transformed with the 5' half of the Barley Yellow Dwarf Virus-PAV genome. Phytopathology 88, 1013–1019.

6) Lagudah, E. S., Appels, R., Brown, A. H. D. and McNeil, D. (1991) The molecular-genetic analysis of *Triticum tauschii*-the D genome donor to hexaploid wheat. Genome 34, 375–386.

7) Larkin, P. J., Young, M. J., Gerlach, W. L. and Waterhouse, P. M. (1991) The Yd2 resistance to barley yellow dwarf virus is effective in barley plants but not in their leaf protoplasts. Ann. Appl. Biol. 118, 115–125.

8) Lister, R. M. and Ranieri, R. (1995) Distribution and economic importance of barley yellow dwarf. In: Barley yellow dwarf: 40 years of progress. (D'Arcy, C. J. and Burnett, P. A., eds) APS press, St Paul, Minn., pp 29–53.

9) Mayo, M. A. and D'Arcy, C. J. (1999) Family Luteoviridae: a Reclassification of Luteoviruses. In: The Luteoviridae. (Smith, H. G. and Barker, H., eds) CABI publishing, Wallingford, UK, pp 15–22.

10) Martin, R. R., Keese, P. M., Young, M., Waterhouse, P. M.& Gerlach, W. L. (1990). Evolution and molecular biology of luteoviruses. Annual Review of Phytopathology, 28, 341–363.

11) Martin, R. R. and D'Arcy, C. J. (1995) Taxonomy of barley yellow dwarf viruses. In: Barley yellow dwarf: 40 years of progress. (D'Arcy, C. J. and Burnett, P. A., eds) APS press, St Paul, Minn., pp 203–214.

12) McGrath, P. F., Vincent, J. R., Lei, C. H., Pawlowski, W. P., Torbert, K. A., Gu, W., Kaeppler, H. F., Wan, Y., Lemaux, P. G., Rines, H. R., Somers, D. A., Larkins, B. A. and Lister, R. M. (1997) Coat protein-mediated resistance to isolates of barley yellow dwarf in oats and barley. Eur. J. Plant Pathol. 103, 695–710.

13) Miller, W. A., Waterhouse, P. M. and Gerlach, W. L. (1988) Sequence and organization of barley yellow dwarf virus genomic RNA. Nucleic Acids Res. 16, 6097–6111.

14) Miller, W. A., Dinesh-Kumar, S. P. and Paul, C. P. (1995) Luteovirus gene expression. Crit. Rev. Plant Sci. 14, 179–211.

15) Paltridge, N. G., Collins, N. C., Bendahmane, A. and Symons, R. H. (1998) Development of YLM, a codominant PCR marker closely linked to the Yd2 gene for resistance to barley yellow dwarf disease. Theor. Appl. Genet. 96, 1170–1177.

16) Presting, G. G., Smith, O. P. and Brown, C. R. (1995) Resistance to potato leafroll virus in potato plants transformed with the coat protein or with vector control constructs. Phytopathology 85, 436–441.

17) Pruss, G., Xin, G., Shi, X. M., Carrington, J. C., Vance, V. B., Ge, X. and Shi, X. M. (1997) Plant viral synergism: the potyviral genome encodes a broad-range pathogenicity enhancer that transactivates replication of heterologous viruses. Plant Cell 9, 859–868.

18) Rasmusson, D. C. and Schaller, C. W. (1959) The inheritance of resistance in barley to the yellow-dwarf virus. Agron. J. 51, 661–664.

19) Sambrook, J., Fritsch, E. F. and Maniatis, T. (1989) Molecular Cloning: A Laboratory Manual, 2$^{nd}$ Edn., Cold Spring Harbor Laboratory Press, Cold Spring Harbor, N.Y.

20) Schaller, C. W., Qualset, C. O. and Rutger, J. N. (1964) Inheritance and linkage of the Yd2 gene conditioning resistance to barley yellow dwarf virus disease in barley. Crop Sci. 4, 544–548.

21) Schaller, C. W. (1984) The genetics of resistance to barley yellow dwarf virus in barley. In: Barley Yellow Dwarf: The Proceedings of a Workshop. (Burnett, P. A., ed) CIMMYT, Mexico, pp. 93–99.

22) Sharp, P. A and Zamore, P. D. (2000) RNA interference. Science 287, 2431–2433.

23) Shi, X. M., Miller, H., Verchot, J., Carrington, J. C., Vance, V. B. and Shi, X. M. (1997) Mutations in the region encoding the central domain of helper component-proteinase (HC-Pro) eliminate potato virus X/potyviral synergism. Virology 231, 35–42.

24) Singh, R. P., Burnett, P. A., Albarran, M. and Rajaram, S. (1993) Bdvl: A gene for tolerance to barley yellow dwarf virus in bread wheats. Crop Sci. 33, 231–234.

25) Smith, N. A., Singh, S. P., Wang, M -B., Stoutjesdijk, P., Green, A. and Waterhouse, P. M. (2000) Total silencing by intron-spliced hairpin RNAs. Nature 407, 319–320.

26) Tingay, S., McElroy, D., Kalla, R., Fieg, S., Wang, M -B., Thornton, S. and Brettell, R. (1997) *Agrobacterium tumefaciens*-mediated barley transformation. Plant Journal 11, 369–1376.

27) Tuschl, T., Zamore, P. D., Lehmann, R., Bartel, D. P. and Sharp, P. A. (1999) Targeted mRNA degradation by double-stranded RNA in vitro. Genes & Development 13, 3191–3197.

28) Vance, V. B. (1991) Replication of potato virus X RNA is altered in coinfections with potato virus Y. Virology 182, 486–494.

29) Vance, V. B., Berger, P. H., Carrington, J. C., Hunt, A. G. and Shi, X. M. (1995) 5' proximal potyvirus sequences mediate potato virus X/potyviral synergistic disease in transgenic tobacco. Virology 206, 583–590.

30) Voinnet, O., Pinto, Y. M and Baulcombe, D. C. (1999) Suppression of gene silencing: A general strategy used by diverse DNA and RNA viruses of plants. Proc. Natl. Acad. Sci. USA 96, 14147–14152.

31) Wang, M -B., Cheng, Z., Keese, P., Graham, M. W., Larkin, P. J. and Waterhouse, P. M. (1998a) Comparison of the coat protein, movement protein and RNA polymerase sequences of Australian, Chinese, and American isolates of barley yellow dwarf virus transmitted by *Rhopalosiphum padi*. Arch. Virol. 143, 1005–1013.

32) Wang, M -B., Li, Z., Matthews, P. R., Upadhyaya, N. M. and Waterhouse, P. M. (1998b) Improved vectors for *Agrobacterium tumefaciens*-mediated transformation of monocot plants. Acta Hort. 461, 401–407.

33) Wang, M -B. and Waterhouse, P. M. (2000) High efficiency silencing of a β-glucuronidase gene in rice is correlated with repetitive transgene structure but independent of DNA methylation. Plant Molecular Biology 43, 67–82.

34) Waterhouse, P. M., Gerlach, W. L. and Miller, W. A. (1986) Serotype-specific and general luteovirus probes from cloned cDNA sequences of barley yellow dwarf virus. J. Gen. Virology 67, 1273–1281.

35) Waterhouse, P. M., Gildow, F. E. and Johnstone, G. R. (1988). The Luteovirus Group, AAB Descriptions of Plant Viruses No. 339. Institute of Horticultural Research, Wellesbourne, Warwick, United Kingdom.

36) Waterhouse, P. M., Graham, M. W. and Wang, M.-B. (1998) Virus resistance and gene silencing in plants can be induced by simultaneous expression of sense and antisense RNA. Proc. Natl. Acad. Sci. USA 95, 13959–13964.

37) Waterhouse, P. M. and Upadhyaya, M. N. (1998) Genetic engineering of virus resistance. In: Molecular Biology of Rice (Shimamoto, K., ed) Springer-Verlag, Tokyo. pp. 257–281.

38) Waterhouse, P. M., Smith, N. A. and Wang, M -B. (1999) Virus resistance and gene silencing: killing the messenger. Trends in Plant Science 4, 452–457.

39) Xin, Z. Y., Brettell, R. I. S., Cheng, Z. M., Waterhouse, P. M., Appels, R., Banks, P. M., Zhou, G. H., Chen, X and Larkin, P. J. (1988) Characterization of a potential source of barley yellow dwarf virus resistance for wheat. Genome 30, 250–257.

40) Zamore, P. D., Tuschl, T., Sharp, P. and Bartel, D. P. (2000) RNAi: double-stranded RNA directs the ATP-dependent cleavage of mRNA at 21 to 23 nucleotide intervals. Cell 101, 25–33.

41) Christensen and Quail (1996) Transgenic Research 5, 213–218

What is claimed is:

1. A non-naturally occurring DNA molecule comprising a plant-expressible promoter, a transcription termination and polyadenylation signal; and a DNA region encoding a first nucleotide sequence of at least 19 nucleotides wherein said first nucleotide sequence has 100% nucleotide sequence identity to a sequence in the sense nucleotide sequence encoding an RNA dependent RNA polymerase of a BYDV isolate; and a second nucleotide sequence that has 100% nucleotide sequence identity to the complement of said first nucleotide sequence; wherein, when said DNA region is transcribed in the cells of a cereal plant, said first and second nucleotide sequences hybridize to form a double stranded RNA.

2. The DNA molecule of claim 1, wherein said sense nucleotide sequence is encoded by the nucleotide sequence of SEQ ID NO: 1 from the nucleotide at position 1 to the nucleotide at position 1014.

3. The DNA molecule of claim 1, wherein said sense nucleotide sequence is encoded by the nucleotide sequence of SEQ ID NO: 1 and said second nucleotide sequence is encoded by the complement of the nucleotide sequence of SEQ ID NO: 1.

4. The DNA molecule of claim 1, wherein said DNA region when transcribed in the cells of a cereal plant yields an RNA molecule comprising a nucleotide spacer between said first nucleotide sequence and said second nucleotide sequence.

5. The DNA molecule of claim 4, wherein said spacer is encoded by the nucleotide sequence of SEQ ID NO: 2.

6. A non-naturally occurring DNA molecule comprising a plant-expressible promoter, a transcription termination and polyadenylation signal; and a DNA region encoding: a first nucleotide sequence of at least 19 nucleotides wherein said first nucleotide sequence has 100% nucleotide sequence identity to a sequence in the sense nucleotide sequence encoding an RNA dependent RNA polymerase of a BYDV isolate, and comprising at least one and maximally 10 additional nucleotide sequences, each of said additional nucleotide sequences having at least 19 nucleotides wherein each additional nucleotide sequence has 100% sequence identity to a sequence in the sense nucleotide sequence of a BYDV isolate genomic sequence or a CYDV isolate genomic sequence; and a second nucleotide sequence complementary to said first nucleotide sequence; wherein, when said DNA region is transcribed in the cells of a cereal plant, said first and second nucleotide sequences hybridize to form a double stranded RNA.

7. The DNA molecule of claim 6, wherein said DNA region comprises in order:

a nucleic acid comprising the nucleotide sequence of SEQ ID No 7 from the nucleotide at position 2314 to the nucleotide at position 2514;

a nucleic acid comprising the nucleotide sequence of SEQ ID No 7 from the nucleotide at position 429 to the nucleotide at position 629;

a nucleic acid comprising the nucleotide sequence of SEQ ID No 7 from the nucleotide at position 5052 to the nucleotide at position 5270;

a nucleic acid comprising the nucleotide sequence of SEQ ID No 8; and a nucleic acid comprising the nucleotide sequence of SEQ ID No 9.

8. A method for producing a cereal plant resistant to a Barley Yellow Dwarf virus comprising the steps of:

producing a population of transgenic cereal plant lines comprising the DNA molecule of any one of claims 1 to 7 integrated into the genome of the cells of transgenic plants of said plant lines; and isolating a transgenic cereal plant line resistant to Barley Yellow Dwarf virus infection.

9. The method of claim 8, wherein said cereal plant is selected from the group of wheat, barley and oats.

10. The method of claim 8, wherein said cereal plant is barley.

11. A method for producing a cereal plant resistant to a Barley Yellow Dwarf virus comprising the steps of producing a population of transgenic cereal plant lines comprising the DNA molecule of any one of claims 1 to 7 integrated into the genome of the cells of transgenic plants of said plant lines;

isolating a transgenic cereal plant resistant to Barley Yellow Dwarf virus infection; and crossing the isolated transgenic cereal plant resistant to Barley Yellow Dwarf virus infection with another cereal plant to obtain progeny plants comprising the DNA molecule of any of claims 1 to 7.

12. A method for producing a cereal plant resistant to a Barley Yellow Dwarf virus in the presence of co-infecting virus, comprising the steps of:

producing a population of transgenic cereal plant lines comprising the DNA molecule of any one of claims 1 to 7 integrated into the genome of the cells of transgenic plants of said plant lines; and isolating a transgenic cereal plant that is resistant to Barley Yellow Dwarf virus infection in the presence of said co-infecting virus.

13. The method of claim 12, wherein said co-infecting virus is Cereal Yellow Dwarf virus.

14. A transgenic cereal plant comprising stably integrated into the genome of the cells of said plant the DNA molecule according to any one of claims 1 to 7 and wherein said cereal plant is resistant to BYDV virus infection and replication of said virus.

15. The cereal plant of claim 14 wherein said plant is selected from the group consisting of wheat, barley, rye and oats.

16. The cereal plant of claim 15 wherein said plant is barley.

17. The method of claim 9, wherein said cereal plant is wheat.

18. The method of claim 9, wherein said cereal plant is oats.

19. The cereal plant of claim 15 wherein said plant is wheat.

20. The cereal plant of claim 15 wherein said plant is oats.

* * * * *